Figure 1:
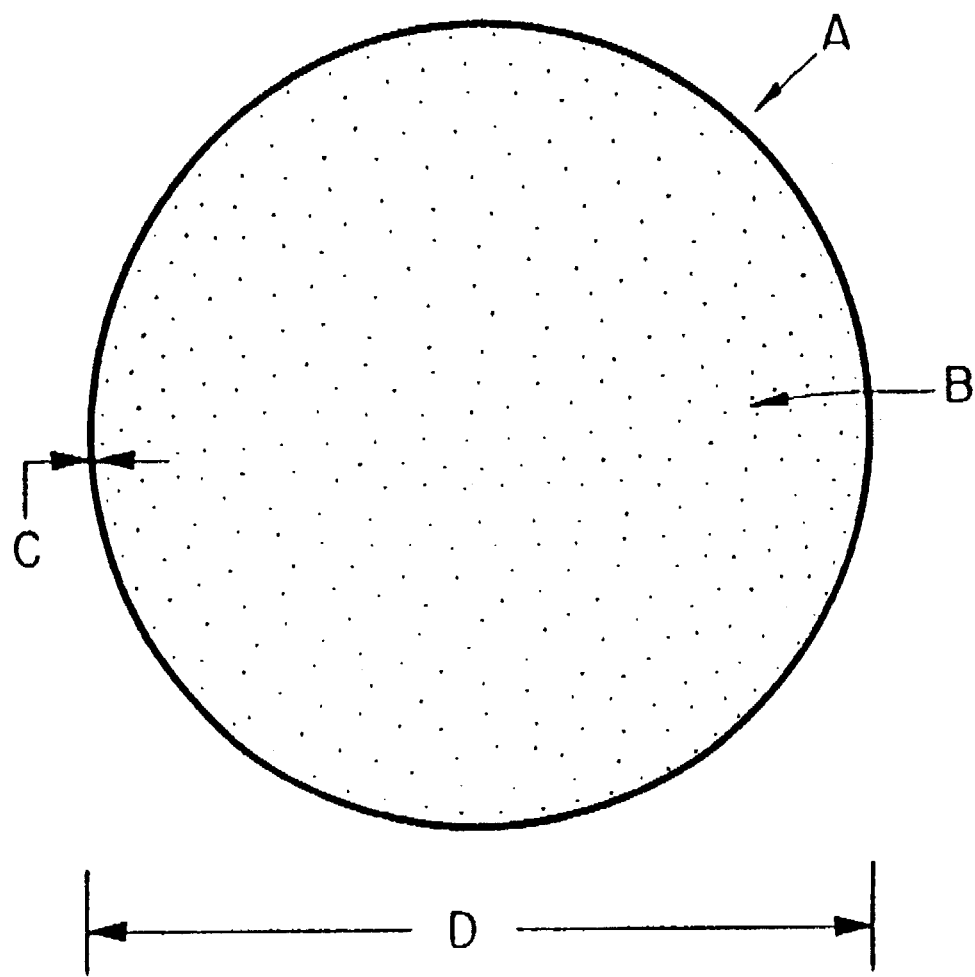

United States Patent [19]
Grinstaff et al.

[11] Patent Number: 5,635,207
[45] Date of Patent: Jun. 3, 1997

[54] METHODS FOR THE PREPARATION OF BLOOD SUBSTITUTES FOR IN VIVO DELIVERY

[75] Inventors: Mark W. Grinstaff, Pasadena; Patrick Soon-Shiong, Los Angeles, both of Calif.; Michael Wong, Champaign, Ill.; Paul A. Sandford, Los Angeles, Calif.; Kenneth S. Suslick, Champaign, Ill.; Neil P. Desai, Los Angeles, Calif.

[73] Assignee: Vivorx Pharmaceuticals, Inc., Santa Monica, Calif.

[21] Appl. No.: 480,621

[22] Filed: Jun. 7, 1995

Related U.S. Application Data

[60] Division of Ser. No. 200,235, Feb. 22, 1994, Pat. No. 5,498,421, which is a continuation-in-part of Ser. No. 23,698, Feb. 22, 1993, Pat. No. 5,439,686, and a continuation-in-part of Ser. No. 35,150, Mar. 26, 1993, Pat. No. 5,362,478.

[51] Int. Cl.$^6$ ..................................................... A61K 9/127
[52] U.S. Cl. ............................ 424/450; 424/489; 424/1.17
[58] Field of Search ................................. 424/1.17, 450, 424/489

[56] References Cited

U.S. PATENT DOCUMENTS

| | | | |
|---|---|---|---|
| 4,073,943 | 2/1978 | Wretlind et al. | 424/358 |
| 4,558,032 | 12/1985 | Ecanow et al. | 514/2 |
| 4,671,954 | 6/1987 | Goldberg et al. | 424/450 |
| 5,439,686 | 8/1995 | Desai et al. | 424/451 |

*Primary Examiner*—Thurman K. Page
*Assistant Examiner*—William E. Benston, Jr.
*Attorney, Agent, or Firm*—Gray Cary Ware & Freidenrich; Stephen E. Reiter

[57] ABSTRACT

In accordance with the present invention, there are provided compositions useful for the in vivo delivery of a biologic, wherein the biologic is associated with a polymeric shell formulated from a biocompatible material. The biologic can be associated with the polymeric shell itself, and/or the biologic, optionally suspended/dispersed in a biocompatible dispersing agent, can be encased by the polymeric shell. In another aspect, the biologic associated with polymeric shell is administered to a subject, optionally dispersed in a suitable biocompatible liquid.

44 Claims, 3 Drawing Sheets

METHODS FOR THE PREPARATION OF BLOOD SUBSTITUTES FOR IN VIVO DELIVERY

RELATED APPLICATIONS

This application is a divisional of application U.S. Ser. No. 08/200,235, filed Feb. 22, 1994, U.S. Pat. No. 5,498,421 which is a continuation-in-part of U.S. Ser. No. 08/023,698, filed Feb. 22, 1993, U.S. Pat. No. 5,439,686 and a continuation-in-part of U.S. Ser. No. 08/035,150, filed Mar. 26, 1993, U.S. Pat. No. 5,362,478 the entire contents of which are hereby incorporated by reference.

FIELD OF THE INVENTION

The present invention relates to in vivo delivery of biologics. In one aspect, biologic is associated with a polymeric shell formulated from a biocompatible material. The biologic can be associated with the polymeric shell itself, and/or the biologic, optionally suspended/dispersed in a biocompatible dispersing agent, can be encased by the polymeric shell. In another aspect, the biologic associated with polymeric shell is administered to a subject, optionally dispersed in a suitable biocompatible liquid.

BACKGROUND OF THE INVENTION

Microparticles and foreign bodies present in the blood are generally cleared from the circulation by the 'blood filtering organs', namely the spleen, lungs and liver. The particulate matter contained in normal whole blood comprises red blood cells (typically 8 microns in diameter), white blood cells (typically 6-8 microns in diameter), and platelets (typically 1-3 microns in diameter). The microcirculation in most organs and tissues allows the free passage of these blood cells. When microthrombii (blood clots) of size greater than 10-15 microns are present in circulation, a risk of infarction or blockage of the capillaries results, leading to ischemia or oxygen deprivation and possible tissue death. Injection into the circulation of particles greater than 10-15 microns in diameter, therefore, must be avoided. A suspension of particles less than 7-8 microns, is however, relatively safe and has been used for the delivery of pharmacologically active agents in the form of liposomes and emulsions, nutritional agents, and contrast media for imaging applications.

The size of particles and their mode of delivery determines their biological behavior. Strand et al. [in *Microspheres-Biomedical Applications*, ed. A. Rembaum, pp 193-227, CRC Press (1988)] have described the fate of particles to be dependent on their size. Particles in the size range of a few nanometers (nm) to 100 nm enter the lymphatic capillaries following interstitial injection, and phagocytosis may occur within the lymph nodes. After intravenous/intraarterial injection, particles less than about 2 microns will be rapidly cleared from the blood stream by the reticuloendothelial system (RES), also known as the mononuclear phagocyte system (MPS). Particles larger than about 7 microns will, after intravenous injection, be trapped in the lung capillaries. After intraarterial injection, particles are trapped in the first capillary bed reached. Inhaled particles are trapped by the alveolar macrophages.

Pharmaceuticals that are water-insoluble or poorly water-soluble and sensitive to acid environments in the stomach cannot be conventionally administered (e.g., by intravenous injection or oral administration). The parenteral administration of such pharmaceuticals has been achieved by emulsification of oil solubilized drug with an aqueous liquid (such as normal saline) in the presence of surfactants or emulsion stabilizers to produce stable microemulsions. These emulsions may be injected intravenously, provided the components of the emulsion are pharmacologically inert. For example, U.S. Pat. No. 4,073,943 describes the administration of water-insoluble pharmacologically active agents dissolved in oils and emulsified with water in the presence of surfactants such as egg phosphatides, pluronics (copolymers of polypropylene glycol and polyethylene glycol), polyglycerol oleate, etc. PCT International Publication No. WO85/00011 describes pharmaceutical microdroplets of an anaesthetic coated with a phospholipid, such as dimyristoyl phosphatidylcholine, having suitable dimensions for intradermal or intravenous injection.

Protein microspheres have been reported in the literature as carriers of pharmacological or diagnostic agents. Microspheres of albumin have been prepared by either heat denaturation or chemical crosslinking. Heat denatured microspheres are produced from an emulsified mixture (e.g., albumin, the agent to be incorporated, and a suitable oil) at temperatures between 100° C. and 150° C. The microspheres are then washed with a suitable solvent and stored. Leucuta et al. [International Journal of Pharmaceutics Vol. 41:213-217 (1988)] describe the method of preparation of heat denatured microspheres.

The procedure for preparing chemically crosslinked microspheres involves treating the emulsion with glutaraldehyde to crosslink the protein, followed by washing and storage. Lee et al. [Science Vol. 213:233-235 (1981)] and U.S. Pat. No. 4,671,954 teach this method of preparation.

The above techniques for the preparation of protein microspheres as carriers of pharmacologically active agents, although suitable for the delivery of water-soluble agents, are incapable of entrapping water-insoluble ones. This limitation is inherent in the technique of preparation which relies on crosslinking or heat denaturation of the protein component in the aqueous phase of a water-in-oil emulsion. Any aqueous-soluble agent dissolved in the protein-containing aqueous phase may be entrapped within the resultant crosslinked or heat-denatured protein matrix, but a poorly aqueous-soluble or oil-soluble agent cannot be incorporated into a protein matrix formed by these techniques.

Thus, the poor aqueous solubility of many biologics presents a problem for human administration. Indeed, the delivery of pharmacologically active agents that are inherently insoluble or poorly soluble in aqueous medium can be seriously impaired if oral delivery is not effective. Accordingly, currently used formulations for the delivery of pharmacologically active agents that are inherently insoluble or poorly soluble in aqueous medium require the addition of agents to solubilize the pharmacologically active agent. Frequently, however, severe allergic reactions are caused by the agents (e.g., emulsifiers) employed to solubilize pharmacologically active agents. Thus, a common regimen of administration involves treatment of the patient with antihistamines and steroids prior to injection of the pharmacologically active agent to reduce the allergic side effects of the agents used to aid in drug delivery.

In an effort to improve the water solubility of drugs that are inherently insoluble or poorly soluble in aqueous medium, several investigators have chemically modified the structure of drugs with functional groups that impart enhanced water-solubility. Among chemical modifications described in the art are the preparation of sulfonated derivatives [Kingston et al., U.S. Pat. No. 5,059,699 (1991)], and amino acid esters [Mathew et al., J. Med. Chem. Vol.

35:145-151 (1992)] which show significant biological activity. Modifications to produce water-soluble derivatives facilitate the intravenous delivery, in aqueous medium (dissolved in an innocuous carrier such as normal saline), of drugs that are inherently insoluble or poorly soluble. Such modifications, however, add to the cost of drug preparation, may induce undesired side-reactions and/or allergic reactions, and/or may decrease the efficiency of the drug.

Among the biologics which are frequently difficult to deliver is oxygen. Indeed, the need for clinically safe and effective oxygen carrying media for use as red blood cell substitutes ("blood substitutes" or "artificial blood") cannot be overemphasized. Some of the potential uses of such media include (a) general transfusion uses, including both routine and emergency situations to replace acute blood loss, (b) support of organs in vitro prior to transplantation or in vivo during surgery, (c) enhancing oxygen delivery to ischemic tissues and organs in vivo, (d) enhancing oxygen delivery to poorly vascularized tumors to increase the treatment efficacy of radiation therapy or chemotherapy, (e) support of organs or animals during experimental investigations, and (f) increased oxygen transport to living cells in culture media.

Blood transfusions are used to supplement the hemodynamic system of patients who suffer from a variety of disorders, including diminished blood volume, or hypovolemia (e.g. due to bleeding), a decreased number of blood cells (e.g. due to bone marrow destruction), or impaired or damaged blood cells (e.g. due to hemolytic anemia). Blood transfusions serve not only to increase the intravascular volume, but also to supply red blood cells which carry dissolved oxygen and facilitate oxygen delivery to tissues.

In the case of transfusion of patients who have experienced significant blood loss, careful matching of donor and recipient blood types often subjects the patient to periods of oxygen deprivation which is detrimental. Furthermore, even when autologous, patient-donated, red blood cells are available through previous phlebotomy and storage, the oxygen-carrying capacity and safety of these autologous cells declines as a consequence of storage. Consequently, for a period of as much as 24 hours after transfusion, the patient may be subject to sub-optimal oxygen delivery. Finally, there is the ever-present danger to the patient of viral and/or bacterial contamination in all transfusions of whole blood and red cells derived therefrom.

Thus, there is a recognized need for a substance that is useful for oxygen transport and delivery under normal environmental conditions that incorporates the following features. Ideally, a substance employed for oxygen transport and delivery will be capable of carrying and delivering oxygen to devices, organs and tissues such that normal oxygen tensions may be maintained in these environments. Such a substance will ideally be safe and non-toxic, free of bacterial and/or viral contamination, and non-antigenic and non-pyrogenic (i.e. less than 0.25 EU/ml). In addition, the substance employed for oxygen transport and delivery will have viscosity, colloid and osmotic properties comparable to blood. It is also desirable that such a substance will be retained in the vascular system of the patient for a long period of time, thus permitting erythropoiesis and maturation of the patient's own red blood cells. Furthermore, it is desirable that the substance employed not interfere with or hinder erythropoiesis.

Currently, a number of intravenous fluids are available for the treatment of acute hypovolemia, including crystalloids, such as lactated Ringer's solution or normal saline, and colloidal solutions, such as normal human serum albumin. Crystalloids and colloids temporarily correct the volume deficit, but do not directly supplement oxygen delivery to tissues. While blood transfusion is the preferred mode of treatment, availability of sufficient quantities of a safe supply of blood is a perpetual problem.

Additional biologics which are frequently inherently insoluble or poorly soluble in aqueous medium, and which are desirable to administer dissolved in an innocuous carrier such as normal saline, while promoting a minimum of undesired side-reactions and/or allergic reactions, are diagnostic agents such as contrast agents. Contrast agents are desirable in radiological imaging because they enhance the visualization of organs (i.e., their location, size and conformation) and other cellular structures from the surrounding medium. The soft tissues, for example, have similar cell composition (i.e., they are primarily composed of water) even though they may have remarkably different biological functions (e.g., liver and pancreas).

The technique of magnetic resonance imaging (MRI) or nuclear magnetic resonance (NMR) imaging relies on the detection of certain atomic nuclei at an applied magnetic field strength using radio-frequency radiation. In some respects it is similar to X-ray computer tomography (CT), in that it can provide (in some cases) cross-sectional images of organs with potentially excellent soft tissue resolution. In its current use, the images constitute a distribution map of protons in organs and tissues. However, unlike X-ray computer tomography, MRI does not use ionizing radiation. MRI is, therefore, a safe non-invasive technique for medical imaging.

While the phenomenon of NMR was discovered in 1954, it is only recently that it has found use in medical diagnostics as a means of mapping internal structure. The technique was first developed by Lauterbur [Nature 242:190–191 (1973)].

It is well known that nuclei with the appropriate nuclear spin align in the direction of the applied magnetic field. The nuclear spin may be aligned in either of two ways: with or against the external magnetic field. Alignment with the field is more stable; while energy must be absorbed to align in the less stable state (i.e. against the applied field). In the case of protons, these nuclei precess or resonate at a frequency of 42.6 MHz in the presence of a 1 tesla (1 tesla=$10^4$ gauss) magnetic field. At this frequency, a radio-frequency (RF) pulse of radiation will excite the nuclei and change their spin orientation to be aligned against the applied magnetic field. After the RF pulse, the excited nuclei "relax" or return to equilibrium or alignment with the magnetic field. The decay of the relaxation signal can be described using two relaxation terms. $T_1$, the spin-lattice relaxation time or longitudinal relaxation time, is the time required by the nuclei to return to equilibrium along the direction of the externally applied magnetic field. The second, $T_2$, or spin-spin relaxation time, is associated with the dephasing of the initially coherent precession of individual proton spins. The relaxation times for various fluids, organs and tissues in different species of mammals is well documented.

One advantage of MRI is that different scanning planes and slice thicknesses can be selected without loss of resolution. This permits high quality transverse, coronal and sagittal images to be obtained directly. The absence of any mechanical moving parts in the MRI equipment promotes a high degree of reliability. It is generally believed that MRI has greater potential than X-ray computer tomography (CT) for the selective examination of tissues. In CT, the X-ray attenuation coefficients alone determine the image contrast, whereas at least three separate variables ($T_1$, $T_2$, and nuclear spin density) contribute to the magnetic resonance image.

Due to subtle physio-chemical differences among organs and tissue, MRI may be capable of differentiating tissue types and in detecting diseases that may not be detected by X-ray or CT. In comparison, CT and X-ray are only sensitive to differences in electron densities in tissues and organs. The images obtainable by MRI techniques can also enable a physician to detect structures smaller than those detectable by CT, due to its better spatial resolution. Additionally, any imaging scan plane can be readily obtained using MRI techniques, including transverse, coronal and sagittal.

Currently, MRI is widely used to aid in the diagnosis of many medical disorders. Examples include joint injuries, bone marrow disorders, soft tissue tumors, mediastinal invasion, lymphadenopathy, cavernous hemangioma, hemochromatosis, cirrhosis, renal cell carcinoma, uterine leiomyoma, adenomyosis, endometriosis, breast carcinomas, stenosis, coronary artery disease, aortic dissection, lipomatous hypertrophy, atrial septum, constrictive pericarditis, and the like [see, for example, Edelman & Warach, Medical Progress 328:708–716 (1993); Edelman & Warach, New England J. of Medicine 328:785–791 (1993)].

Routinely employed magnetic resonance images are presently based on proton signals arising from the water molecules within cells. Consequently, it is often difficult to decipher the images and distinguish individual organs and cellular structures. There are two potential means to better differentiate proton signals. The first involves using a contrast agent that alters the $T_1$ or $T_2$ of the water molecules in one region compared to another. For example, gadolinium diethylenetriaminepentaacetic acid (Gd-DTPA) shortens the proton $T_1$ relaxation time of water molecules in near proximity thereto, thereby enhancing the obtained images.

Paramagnetic cations such as, for example, Gd, Mn, and Fe are excellent MRI contrast agents, as suggested above. Their ability to shorten the proton $T_1$ relaxation time of the surrounding water enables enhanced MRI images to be obtained which otherwise would be unreadable.

The second route to differentiate individual organs and cellular structures is to introduce another nucleus for imaging (i.e., an imaging agent). Using this second approach, imaging can only occur where the contrast agent has been delivered. An advantage of this method is the fact that imaging is achieved free from interference from the surrounding water. Suitable contrast agents must be biocompatible (i.e. non-toxic, chemically stable, not reactive with tissues) and of limited lifetime before elimination from the body.

Although, hydrogen has typically been selected as the basis for MRI scanning (because of its abundance in the body), this can result in poorly imaged areas due to lack of contrast. Thus the use of other active MRI nuclei (such as fluorine) can, therefore, be advantageous. The use of certain perfluorocarbons in various diagnostic imaging technologies such as ultrasound, magnetic resonance, radiography and computer tomography has been described in an article by Mattery [see SPIE, 626, XIV/PACS IV, 18–23 (1986)]. The use of fluorine is advantageous since fluorine is not naturally found within the body.

Prior art suggestions of fluorine-containing compounds useful for magnetic resonance imaging for medical diagnostic purposes are limited to a select group of fluorine-containing molecules that are water soluble or can form emulsions. Accordingly, prior art use of fluorocarbon emulsions of aqueous soluble fluorocarbons suffers from numerous drawbacks, for example, 1) the use of unstable emulsions, 2) the lack of organ specificity and targeting, 3) the potential for inducing allergic reactions due to the use of emulsifiers and surfactants (e.g., egg phophatides and egg yolk lecithin), 4) limited delivery capabilities, and 5) water soluble fluorocarbons are quickly diluted in blood after intravenous injection.

BRIEF DESCRIPTION OF THE INVENTION

In accordance with the present invention, there are provided compositions useful for in vivo delivery of biologics, in the form of microparticles that are suitable for parenteral administration in aqueous suspension. Invention compositions comprise biologic (as a solid, liquid or gas) associated with a polymeric shell. The polymeric shell is a biocompatible material, crosslinked by the presence of disulfide bonds. The polymeric shell associated with biologic is optionally suspended in a biocompatible medium for administration. Use of invention compositions for the delivery of biologics obviates the necessity for administration of biologics in an emulsion containing, for example, ethanol and polyethoxylated castor oil, diluted in normal saline (see, for example, Norton et al., in Abstracts of the 2nd National Cancer Institute Workshop on Taxol & Taxus, Sep. 23–24, 1992). A disadvantage of such known compositions is their propensity to produce allergic side effects.

In accordance with another aspect of the present invention, it has surprisingly and unexpectedly been discovered that insoluble constructs of the protein hemoglobin (Hb) prepared in accordance with the invention reversibly bind oxygen. Insoluble hemoglobin constructs (IHC) of the present invention bind oxygen with oxygen affinities similar to those obtained with soluble hemoglobin molecules in red blood cells, or soluble modified hemoglobin molecules that have been described in the prior art as potential blood substitutes.

In accordance with yet another aspect of the present invention, there are provided methods for entrapping biologics in a polymeric shell. Still further in accordance with the present invention, there are provided means for obtaining local oxygen and temperature data, and for obtaining fluorine magnetic resonance images of body organs and tissues.

The delivery of biologics in the form of a microparticulate suspension allows some degree of targeting to organs such as the liver, lungs, spleen, lymphatic circulation, and the like, through the use of particles of varying size, and through administration by different routes. The invention method of delivery further allows the administration of biologics, such as substantially water insoluble pharmacologically active agents, employing a much smaller volume of liquid and requiring greatly reduced administration time relative to administration volumes and times required by prior art delivery systems (e.g., intravenous infusion of approximately one to two liters of fluid over a 24 hour period are required to deliver a typical human dose of 200–400 mg of taxol).

For example, a suspension of polymeric shells of the invention can be administered intravenously, making imaging of vascularized organs (e.g., liver, spleen, lymph and lung) and bone marrow possible. Organ target specificity is achieved as a result of uptake of the micron-sized organofluorine-containing polymeric shells by the reticuloendothelial system (RES) (also known as the mononuclear phagocyte (MNP) system). Organs such as the liver and spleen play an important role in removing foreign species (e.g., particulate matter) from the bloodstream, and hence are often referred to as the "blood filtering organs". These organs make up a major part of the RES. In addition, lymph nodes within the lymphatic circulation contain cells of the RES. Consequently, imaging of the lymphatic system is possible employing micron-sized organofluorine-containing polymeric shells of the present invention. Given orally or as a suppository, imaging of the stomach and gastrointestinal tract can be carried out. Such suspensions can also be injected into non-vascular space, such as the cerebro-spinal cavity, allowing imaging of such space as well.

As a further embodiment of the present invention, paramagnetic cations such as Gd, Mn, Fe, and the like can be bound to polyanions, such as alginate, and used as an effective MRI contrast agent.

The present invention overcomes the drawbacks of the prior art by providing 1) injectable suspensions of polymeric shells containing biologic, 2) biologics in a form having enhanced stability compared to simple emulsions, 3) organ targeting specificity (e.g., liver, spleen, lung, and the like) due to uptake of the polymeric shells of the invention by the RES or MNP system, 4) emulsifier-free system, thereby avoiding agents that may potentially cause allergic reactions, and 5) the ability to inject relatively small doses of biologic and still achieve good response because the biologic-containing polymeric shells of the invention can be targeted to a specific organ.

BRIEF DESCRIPTION OF THE FIGURES

FIG. 1 shows a schematic of a polymeric shell prepared in accordance with the present invention. In the Figure, A refers to the insoluble disulfide crosslinked polymeric shell, B refers to the interior of the polymeric shell, which can contain oxygen or other gas, a fluorocarbon containing dissolved oxygen, a biocompatible oil having biologic dissolved therein, a water-in-oil emulsion containing biologic dissolved in aqueous media, a suspension of solid particles dispersed in a liquid, and the like, C designates the thickness of the polymeric shell, typically about 5–50 nanometers, and D refers to the diameter of the polymeric shell, typically in the range of about 0.1 up to 20 μm.

FIG. 2 presents oxygen binding curves (i.e., a graph of Hill coefficient (n) as a function of oxygen partial pressure) for a solution of stroma-free hemoglobin (the dashed line curve) and a solution containing insolubilized hemoglobin constructs of the present invention (the solid line curve). Actual data points with the insolubilized hemoglobin constructs of the present invention are shown as solid boxes.

FIG. 3 presents oxygen binding curves for a solution of stroma-free hemoglobin (the dashed line curve) and a solution containing insolubilized hemoglobin constructs of the present invention (the solid line curve) following treatment with 1.7 mM of the allosteric effector, 2,3-bisphosphoglycerate (2,3-BPG). Actual data points with the insolubilized hemoglobin constructs of the present invention are shown as solid boxes.

DETAILED DESCRIPTION OF THE INVENTION

In accordance with the present invention, there are provided compositions for in vivo delivery of a biologic, wherein said biologic is selected from:

- a solid, optionally dispersed in a biocompatible dispersing agent, substantially completely contained within a polymeric shell,
- a liquid, optionally dispersed in a biocompatible dispersing agent, substantially completely contained within a polymeric shell,
- a gas, optionally dispersed in a biocompatible dispersing agent, substantially completely contained within a polymeric shell,
- a gas associated with a polymeric shell, or mixtures of any two or more thereof, wherein the largest cross-sectional dimension of said shell is no greater than about 10 microns, wherein said polymeric shell comprises a biocompatible material which is substantially crosslinked by way of disulfide bonds, and wherein the exterior of said polymeric shell is optionally modified by a suitable agent, wherein said agent is linked to said polymeric shell through an optional covalent linkage.

As used herein, the term "in vivo delivery" refers to delivery of a biologic by such routes of administration as oral, intravenous, subcutaneous, intraperitoneal, intrathecal, intramuscular, intracranial, inhalational, topical, transdermal, suppository (rectal), pessary (vaginal), and the like.

As used herein, the term "biologic" refers to pharmaceutically active agents (such as analgesic agents, anesthetic agents, anti-asthamatic agents, antibiotics, anti-depressant agents, anti-diabetic agents, anti-fungal agents, anti-hypertensive agents, anti-inflammatory agents, anti-neoplastic agents, anxiolytic agents, enzymatically active agents, nucleic acid constructs, immunostimulating agents, immunosuppressive agents, physiologically active gases, vaccines, and the like), diagnostic agents (such as ultrasound contrast agents, radiocontrast agents, or magnetic contrast agents), agents of nutritional value, and the like.

As used herein, the term "micron" refers to a unit of measure of one one-thousandth of a millimeter.

A number of biocompatible materials may be employed in the practice of the present invention for the formation of a polymeric shell. As used herein, the term "biocompatible" describes a substance that does not appreciably alter or affect in any adverse way, the biological system into which it is introduced. Essentially any material, natural or synthetic, bearing sulfhydryl groups or disulfide bonds within its structure may be utilized for the preparation of a disulfide crosslinked shell. The sulfhydryl groups or disulfide linkages may be preexisting within the structure of the biocompatible material, or they may be introduced by a suitable chemical modification. For example, naturally occurring biocompatible materials such as proteins, polypeptides, oligopeptides, polynucleotides, polysaccharides (e.g., starch, cellulose, dextrans, alginates, chitosan, pectin, hyaluronic acid, and the like), lipids, and so on, are candidates for such modification. Other linkages, such as esters, amides, ethers, and the like, can also be formed during the ultrasonic irradiation step (so long as the requisite functional groups are present on the starting material).

As examples of suitable biocompatible materials, naturally occurring or synthetic proteins may be employed, so long as such proteins have sufficient sulfhydryl or disulfide groups so that crosslinking (through disulfide bond formation, for example, as a result of oxidation during ultrasonic irradiation) can occur. Examples of suitable proteins include albumin (which contains 35 cysteine residues), insulin (which contains 6 cysteines), hemoglobin (which contains 6 cysteine residues per $\alpha_2\beta_2$ unit), lysozyme (which contains 8 cysteine residues), immunoglobulins, α-2-macroglobulin, fibronectin, vitronectin, fibrinogen, and the like, as well as combinations of any two or more thereof.

A presently preferred protein for use in the formation of a polymeric shell is albumin. Another presently preferred protein for use in the formation of a polymeric shell is hemoglobin. Yet another presently preferred protein for use in the formation of a polymeric shell is a combination of albumin and hemoglobin. Optionally, proteins such as $\alpha$-2-macroglobulin, a known opsonin, could be used to enhance uptake of the shell encased particles of biologic by macrophage-like cells, or to enhance the uptake of the shell encased particles into the liver and spleen. Other functional proteins, such as antibodies or enzymes, which could facilitate targetting of biologic to a desired site, can also be used in the formation of the polymeric shell.

Similarly, synthetic polypeptides containing sulfhydryl or disulfide groups are also good candidates for formation of particles having a polymeric shell. In addition, polyalkylene glycols (e.g., linear or branched chain), polyvinyl alcohol, polyhydroxyethyl methacrylate, polyacrylic acid, polyethyloxazoline, polyacrylamide, polyvinyl pyrrolidinone, and the like, are good candidates for chemical modification (to introduce sulfhydryl and/or disulfide linkages) and shell formation (by causing the crosslinking thereof).

In the preparation of invention compositions, one can optionally employ a dispersing agent to suspend or dissolve biologic. Dispersing agents contemplated for use in the practice of the present invention include any liquid that is capable of suspending or dissolving biologic, but does not chemically react with either the polymer employed to produce the shell, or the biologic itself. Examples include water, vegetable oils (e.g., soybean oil, mineral oil, corn oil, rapeseed oil, coconut oil, olive oil, safflower oil, cotton seed oil, and the like), aliphatic, cycloaliphatic, or aromatic hydrocarbons having 4–30 carbon atoms (e.g., n-dodecane, n-decane, n-hexane, cyclohexane, toluene, benzene, and the like), aliphatic or aromatic alcohols having 1–30 carbon atoms (e.g., octanol, and the like), aliphatic or aromatic esters having 2–30 carbon atoms (e.g., ethyl caprylate (octanoate), and the like), alkyl, aryl, or cyclic ethers having 2–30 carbon atoms (e.g., diethyl ether, tetrahydrofuran, and the like), alkyl or aryl halides having 1–30 carbon atoms (and optionally more than one halogen substituent, e.g., $CH_3Cl$, $CH_2Cl_2$, $CH_2Cl-CH_2Cl$, and the like), ketones having 3–30 carbon atoms (e.g., acetone, methyl ethyl ketone, and the like), polyalkylene glycols (e.g., polyethylene glycol, and the like), or combinations of any two or more thereof.

Especially preferred combinations of dispersing agents include volatile liquids such as dichloromethane, ethyl acetate, benzene, and the like (i.e., solvents that have a high degree of solubility for the pharmacologically active agent, and are soluble in the other dispersing agent employed), along with a less volatile dispersing agent. When added to the other dispersing agent, these volatile additives help to drive the solubility of the pharmacologically active agent into the dispersing agent. This is desirable since this step is usually time consuming. Following dissolution, the volatile component may be removed by evaporation (optionally under vacuum).

Particles of biologic substantially completely contained within a polymeric shell, or associated therewith, prepared as described herein, are delivered neat, or optionally as a suspension in a biocompatible medium. This medium may be selected from water, buffered aqueous media, saline, buffered saline, optionally buffered solutions of amino acids, optionally buffered solutions of proteins, optionally buffered solutions of sugars, optionally buffered solutions of carbohydrates, optionally buffered solutions of vitamins, optionally buffered solutions of synthetic polymers, lipid-containing emulsions, and the like.

In accordance with another embodiment of the present invention, there is provided a method for the preparation of a biologic for in vivo delivery, said method comprising subjecting medium containing biocompatible material capable of being crosslinked by disulfide bonds and biologic to high intensity ultrasound conditions for a time sufficient to promote crosslinking of said biocompatible material by disulfide bonds;

wherein said biologic is substantially completely contained within a polymeric shell, and wherein the largest cross-sectional dimension of said shell is no greater than about 10 microns.

Thus, in accordance with the present invention, biologics contained within polymeric shells are synthesized using high intensity ultrasound. Two non-linear acoustic processes are involved in the formation of stable polymeric shells (i.e., acoustic emulsification and cavitation). First, acoustic emulsification disperses the biologic into the aqueous protein solution. The dispersion formed is then chemically crosslinked and stabilized by the formation of disulfide bonds. The disulfide bonds are formed from the cysteine residues (in the case where the polymer is a protein such as albumin) that are oxidized by superoxide which is produced via acoustic cavitation.

The resulting suspension is optionally filtered through centricon filters (100 kDa cutoff) and the filtered constructs or microbubbles are resuspended in normal saline or suitable buffer. FIG. 1 shows a schematic of such a construct. The average diameter of these constructs is approximately 2 microns. Particle size distribution, as determined with an Elzone particle counter, is seen to be quite narrow (a gaussian distribution with a mean diameter of about 3 microns is typically observed). The size range of particles obtained by this technique is between 0.1 micron to 20 microns. A preferred size range is 0.5 to 10 microns and the most preferred range is 1 to 5 microns. This size is ideally suited for medical applications, since intravenous or intraarterial injections can be accomplished without risk of small blood vessel blockage and subsequent tissue (ischemia due to oxygen deprivation) damage. For comparison, normal red blood cells are approximately 8 microns in diameter.

A nonobvious feature of the above-described process is in the choice of dispersing agent, specifically with respect to the polarity of the dispersing agent. The formation of a shell about the particles of biologic involves reorientation of the biocompatible material at the interface between the aqueous and non-aqueous phases such that the hydrophilic regions within the biocompatible material are exposed to the aqueous phase while the hydrophobic regions within the biocompatible material are oriented towards the non-aqueous phase. In the situation where the biocompatible material is a protein, in order to effect unfolding, or change the conformation thereof, energy must be supplied to the polymer. The interfacial free energy (interfacial tension) between the two liquid phases (i.e., aqueous and non-aqueous) contributes to changes in protein conformation at that interface. Thermal energy also contributes to the energy pool required for unfolding and/or change of protein conformation.

Thermal energy input is a function of such variables as the acoustic power employed in the high intensity ultrasonic irradiation process, the high intensity ultrasonic irradiation time, the nature of the material being subjected to high intensity ultrasonic irradiation, the volume of the material being subjected to high intensity ultrasonic irradiation, and the like. The acoustic power of high intensity ultrasonic irradiation processes can vary widely, typically falling in the range of about 1 up to 1000 watts/cm$^2$; with an acoustic power in the range of about 50 up to 200 watts/cm$^2$ being a presently preferred range. Similarly, exposure time to high intensity ultrasonic irradiation can vary widely, typically falling in the range of a few seconds up to about 5 minutes. Preferably, exposure time to high intensity ultrasonic irradiation will fall in the range of about 15 up to 60 seconds. Those of skill in the art recognize that the higher the acoustic power applied, the less exposure time to high intensity ultrasonic irradiation is required, and vice versa.

The interfacial free energy is directly proportional to the polarity difference between the two liquids. Thus at a given operating temperature a minimum free energy at the interface between the two liquids is essential to form the desired polymer shell. Thus, if a homologous series of dispersing agents is taken with a gradual change in polarity, e.g., ethyl esters of alkanoic acids, then higher homologues are increasingly nonpolar, i.e., the interfacial tension between these dispersing agents and water increases as the number of carbon atoms in the ester increases. Thus it is found that, although ethyl acetate is water-immiscible (i.e., an ester of a 2 carbon acid), at room temperature (~20° C.), this dispersing agent alone will not give a significant yield of polymer shell-coated particles. In contrast, a higher ester such as ethyl octanoate (ester of an 8 carbon acid) gives polymer shell-coated particles in high yield. In fact, ethyl heptanoate (ester of a 7 carbon acid) gives a moderate yield while the lower esters (esters of 3, 4, 5, or 6 carbon acids) give poor yield. Thus, at a given temperature, one could set a condition of minimum aqueous-dispersing agent interfacial tension required for formation of high yields of polymer shell-coated particles.

Temperature is another variable that may be manipulated to affect the yield of polymer shell-coated particles. In general the surface tension of a liquid decreases with increasing temperature. The rate of change of surface tension with temperature is often different for different liquids. Thus, for example, the interfacial tension ($\Delta\gamma$) between two liquids may be $\Delta\gamma_1$ at temperature $T_1$ and $\Delta\gamma_2$ at temperature $T_2$. If $\Delta\gamma_1$ at $T_1$ is close to the minimum required to form polymeric shells of the present invention, and if $\Delta\gamma_2$ (at temp. $T_2$) is greater than $\Delta\gamma_1$, then a change of temperature from $T_1$ to $T_2$ will increase the yield of polymeric shells. This, in fact, is observed in the case of ethyl heptanoate, which gives a moderate yield at 20° C. but gives a high yield at 10° C.

Temperature also affects the vapor pressure of the liquids employed. The lower the temperature, the lower the total vapor pressure. The lower the total vapor pressure, the more efficient is the collapse of the cavitation bubble. A more efficient collapse of the ultrasonic irradiation bubble correlates with an increased rate of superoxide ($HO_2^-$) formation. Increased rate of superoxide formation leads to increased yields of polymeric shells at lower temperatures. As a countervailing consideration, however, the reaction rate for oxidation of sulfhydryl groups (i.e., to form disulfide linkages) by superoxide ions increases with increasing temperature. Thus for a given liquid subjected to ultrasonic irradiation conditions, there exists a fairly narrow range of optimum operating temperatures within which a high yield of polymeric shells is obtained.

Thus a combination of two effects, i.e., the change in surface tension with temperature (which directly affects unfolding and/or conformational changes of the polymer) and the change in reaction yield (the reaction being crosslinking of the polymer via formation of disulfide linkages) with temperature dictate the overall conversion or yield of polymer shell-coated particles. Temperatures suitable for the preparation of polymeric shells of the invention fall in the range of about 0°–80° C.

The ultrasonic irradiation process described above may be manipulated to produce polymer shell-coated particles containing biologic having a range of sizes. Presently preferred particle radii fall in the range of about 0.1 up to about 5 micron. A narrow size distribution in this range is very suitable for intravenous delivery of biologic. The polymer shell-coated particles are then preferably suspended in biocompatible medium (as described herein) prior to administration by suitable means.

In addition, the polymeric shell can optionally be modified by a suitable agent, wherein the agent is associated with the polymeric shell through an optional covalent bond. Covalent bonds contemplated for such linkages include ester, ether, urethane, diester, amide, secondary or tertiary amine, phosphate ester, sulfate ester, and the like bonds. Suitable agents contemplated for this optional modification of the polymeric shell include synthetic polymers (polyalkylene glycols (e.g., linear or branched chain polyethylene glycol), polyvinyl alcohol, polyhydroxyethyl methacrylate, polyacrylic acid, polyethyloxazoline, polyacrylamide, polyvinyl pyrrolidinone, and the like), phospholipids (such as phosphatidyl choline (PC), phosphatidyl ethanolamine (PE), phosphatidyl inositol (PI), sphingomyelin, and the like), proteins (such as enzymes, antibodies, and the like), polysaccharides (such as starch, cellulose, dextrans, alginates, chitosan, pectin, hyaluronic acid, and the like), chemical modifying agents (such as pyridoxal 5'-phosphate, derivatives of pyridoxal, dialdehydes, diaspirin esters, and the like), or combinations of any two or more thereof.

Variations on the general theme of dissolved biologic enclosed within a polymeric shell are possible. A suspension of fine particles of biologic in a biocompatible dispersing agent could be used (in place of a biocompatible dispersing agent containing dissolved biologic) to produce a polymeric shell containing dispersing agent-suspended particles of biologic. In other words, the polymeric shell could contain a saturated solution of biologic in dispersing agent. Another variation is a polymeric shell containing a solid core of biologic produced by initially dissolving the biologic in a volatile organic solvent (e.g. benzene), forming the polymeric shell and evaporating the volatile solvent under vacuum, e.g., in a rotary evaporator, or freeze-drying the entire suspension. This results in a structure having a solid core of biologic surrounded by a polymer coat. This latter method is particularly advantageous for delivering high doses of biologic in a relatively small volume. In some cases, the biocompatible material forming the shell about the core could itself be a therapeutic or diagnostic agent, e.g., in the case of insulin, which may be delivered as part of a polymeric shell formed in the ultrasonic irradiation process described above. In other cases, the polymer forming the shell could participate in the delivery of a biologic, e.g., in the case of hemoglobin, which may be delivered as part of a polymeric shell formed in the ultrasonic irradiation process described above, thereby providing a blood substitute having a high binding capacity for oxygen.

Variations in the polymeric shell are also possible. For example, a small amount of PEG containing sulfhydryl groups could be included with the polymer. Upon exposure to ultrasonic irradiation, the PEG is crosslinked into the polymer and forms a component of the polymeric shell.

Alternatively, PEG can be linked to the polymeric shell following the preparation of the shell (rather than being included as part of the media from which the shell is prepared).

PEG is known for its nonadhesive character and has been attached to proteins and enzymes to increase their circulation time in vivo [Abuchowski et al., J. Biol. Chem. Vol. 252:3578 (1977)]. PEG has also been attached to phospholipids forming the lipidic bilayer in liposomes to reduce their uptake and prolong lifetimes in vivo [Klibanov et al., FEBS Letters Vol. 268:235 (1990)]. Thus the incorporation of PEG into the walls of crosslinked protein shells alters their blood circulation time. This property can be exploited to maintain higher blood levels of biologic and prolonged release times for the biologic.

Useful for the modification of the polymeric shell are electrophilic PEG derivatives including PEG-imidazoles, succinimidyl succinates, nitrophenyl carbonates, tresylates, and the like; nucleophilic PEG derivatives including PEG-amines, amino acid esters, hydrazides, thiols, and the like. The PEG-modified polymeric shell will be expected to persist in the circulation for longer periods than their unmodified counterparts. The modification of polymeric shell with PEG may be performed before formation of the shell, or following formation thereof. The currently preferred technique is to modify the polymeric shell after formation thereof. Other polymers including dextran, alginates, hydroxyethyl starch, and the like, may be utilized in the modification of the polymeric shell.

One skilled in the art will recognize that several variations are possible within the scope and spirit of this invention. For example, the dispersing agent within the polymeric shell may be varied, a large variety of biologics may be utilized, and a wide range of proteins as well as other natural and synthetic polymers may be used in the formation of the walls of the polymeric shell. Applications are also fairly wide ranging. Other than biomedical applications such as the delivery of drugs, diagnostic agents (in imaging applications), artificial blood (sonochemically crosslinked hemoglobin) and parenteral nutritional agents, the polymeric shell structures of the invention may be incorporated into cosmetic applications such as skin creams or hair care products, in perfumery applications, in pressure sensitive inks, pesticides, and the like.

In accordance with one embodiment of the present invention, polymeric shells prepared as described above are used for the in vivo delivery of biologics, such as pharmaceutically active agents, diagnostic agents or agents of nutritional value. Examples of pharmacologically active agents contemplated for use in the practice of the present invention include analgesic agents (e.g., acetominophen, aspirin, ibuprofen, morphine and derivatives thereof, and the like), anesthetic gases (e.g., cyclopropane, enfluorane, halothane, isofluorane, methoxyfluorane, nitrous oxide, and the like), anti-asthamatic agents (e.g., azelastine, ketotifen, traxanox, and the like), antibiotics (e.g., neomycin, streptomycin, chloramphenicol, cephalosporin, ampicillin, penicillin, tetracycline, and the like), anti-depressant agents (e.g., nefopam, oxypertine, imipramine, trazadone, and the like), anti-diabetic agents (e.g., biguanidines, hormones, sulfonylurea derivatives, and the like), anti-fungal agents (e.g., amphotericin B, nystatin, candicidin, and the like), anti-hypertensive agents (e.g., propanolol, propafenone, oxyprenolol, nifedipine, reserpine, and the like), steroidal anti-inflammatory agents (e.g., cortisone, hydrocortisone, dexamethasone, prednisolone, prednisone, fluazacort, and the like), non-steroidal anti-inflammatory agents (e.g., indomethacin, ibuprofen, ramifenizone, piroxicam, and the like), anti-neoplastic agents (e.g., adriamycin, cyclophosphamide, actinomycin, bleomycin, duanorubicin, doxorubicin, epirubicin, mitomycin, methotrexate, fluorouracil, carboplatin, carmustine (BCNU), cisplatin, etoposide, interferons, phenesterine, taxol (as used herein, the term "taxol" is intended to include taxol analogs and prodrugs, taxanes, and other taxol-like drugs, e.g., Taxotere, and the like), camptothecin and derivatives thereof (which compounds have great promise for the treatment of colon cancer), vinblastine, vincristine, as well as hormonal anti-neoplastic agents such as estrogens, progestogens, tamoxifen, and the like), anxiolytic agents (e.g., dantrolene, diazepam, and the like), enzymatically active agents (e.g., DNAse, ribozymes, and the like), nucleic acid constructs (e.g., IGF-1 encoding sequence, Factor VIII encoding sequence, Factor IX encoding sequence, antisense nucleotide sequences, and the like), immunostimulating agents (i.e., interleukins, interferons, vaccines, and the like), immunosuppressive agents (e.g., cyclosporine (CsA), azathioprine, mizorobine, FK506, prednisone, and the like), physiologically active gases (e.g., air, oxygen, argon, nitrogen, carbon monoxide, carbon dioxide, helium, xenon, nitrous oxide, nitric oxide, nitrogen dioxide, and the like, as well as combinations of any two or more thereof), as well as other pharmacologically active agents, such as cimetidine, mitotane, visadine, halonitrosoureas, anthracyclines, ellipticine, benzocaine, barbiturates, and the like.

Examples of diagnostic agents contemplated for use in the practice of the present invention include ultrasound contrast agents, radiocontrast agents (e.g., iodo-octanes, halocarbons, renografin, and the like), magnetic contrast agents (e.g., fluorocarbons, lipid soluble paramagnetic compounds, GdDTPA, aqueous paramagnetic compounds, and the like), as well as other agents (e.g., gases such as argon, nitrogen, carbon monoxide, carbon dioxide, helium, xenon, nitrous oxide, nitric oxide, nitrogen dioxide, and the like, as well as combinations of any two or more thereof).

Examples of agents of nutritional value contemplated for use in the practice of the present invention include amino acids, sugars, proteins, carbohydrates, fat-soluble vitamins (e.g., vitamins A, D, E, K, and the like) or fat, or combinations of any two or more thereof.

Key differences between the biologic-containing polymeric shell of the invention and protein microspheres of the prior art are in the nature of formation and the final state of the protein after formation of the polymeric shell, and its ability to carry poorly aqueous-soluble or substantially aqueous-insoluble agents. In accordance with the present invention, the polymer (e.g., a protein) is selectively chemically crosslinked through the formation of disulfide bonds through, for example, the amino acid cysteine that occurs in the natural structure of a number of proteins. An ultrasonic irradiation process is used to disperse a dispersing agent containing dissolved or suspended biologic into an aqueous solution of a biocompatible material bearing sulfhydryl or disulfide groups (e.g., albumin) whereby a shell of crosslinked polymer is formed around fine droplets of non-aqueous medium. The ultrasonic irradiation process produces cavitation in the liquid that causes tremendous local heating and results in the formation of superoxide ions that crosslink the polymer by oxidizing the sulfhydryl residues (and/or disrupting existing disulfide bonds) to form new, crosslinking disulfide bonds.

In contrast to the invention process, the prior art method of glutaraldehyde crosslinking is nonspecific and essentially reactive with any nucleophilic group present in the protein structure (e.g., amines, sulfhydryls and hydroxyls). Heat denaturation as taught by the prior art significantly and irreversibly alters protein structure. In contrast, disulfide formation contemplated by the present invention is very specific, and does not substantially denature the protein. In addition, particles or droplets of biologic contained within a polymeric shell differ from crosslinked or heat denatured protein microspheres of the prior art because the polymeric shell produced by the invention process is relatively thin compared to the diameter of the coated particle. It has been determined (by transmission electron microscopy) that the "shell thickness" of the polymeric coat is approximately 25 nanometers for a coated particle having a diameter of 1 micron (1000 nanometers). In contrast, microspheres of the prior art do not have protein shells, but rather, have protein dispersed throughout the volume of the microsphere.

The polymeric shell containing solid, liquid or gas cores of biologic allows for the delivery of high doses of biologic in relatively small volumes. This minimizes patient discomfort at receiving large volumes of fluid and minimizes hospital stay. In addition, the walls of the polymeric shell are generally completely degradable in vivo by proteolytic enzymes (e.g., when the polymer is a protein), resulting in no side effects from the delivery system, as is frequently the case with current formulations.

According to this embodiment of the present invention, droplets or particles of biologic are contained within a shell having a cross-sectional diameter of no greater than about 10 microns. A cross-sectional diameter of less than 5 microns is more preferred, while a cross-sectional diameter of about 2 microns is presently the most preferred for the intravenous route of administration.

In accordance with another embodiment of the present invention, it has been discovered that polymeric shells as described herein, when prepared from hemoglobin, have surprisingly high oxygen-binding capability, and therefore are useful as blood substitutes. Hemoglobin (Lehninger, in *Biochemistry*, Worth Publishers, Inc., New York, pp. 145–149, 1975) is a 64,500 MW protein that consists of a tetramer (two $\alpha$ and two $\beta$ chains). Each $\alpha$ and $\beta$ chain binds a heme residue in a noncovalent linkage. The $\alpha$ and $\beta$ chains are also held together by noncovalent bonds-resulting from hydrogen bonding and van der Waals forces. The four heme groups, one in each subunit, are capable of binding four molecules of oxygen. These flat heme groups contain an iron atom that is in a square-planar coordination. The four hemes are situated relatively far apart from one another in the intact molecule.

The interaction or cooperation of heme units in binding of oxygen greatly increases the oxygen binding capacity of each heme unit within the tetrameric hemoglobin molecule. In general, a single isolated heme unit would be expected to bind a single molecule of oxygen. However, neighboring heme units within the hemoglobin molecule cooperate to increase the bound oxygen per heme unit. This cooperativity is described in terms of a "Hill Coefficient" whose value reflects the number of interacting oxygen binding sites. In the case of native hemoglobin, the Hill coefficient is approximately 2.8.

Soluble hemoglobin constitutes about 90% of the total protein in red blood cells. 100 ml of whole blood is capable of absorbing approximately 21 ml of gaseous oxygen due to the binding ability of hemoglobin. Equally important to the binding of oxygen, hemoglobin is also efficient in releasing the bound oxygen to tissues. The ability of hemoglobin to bind and release oxygen is often quantitatively expressed as the $P_{50}$ (or $P_{1/2}$). For example, the $P_{50}$ for whole blood, i.e., the partial pressure of oxygen which results in fifty percent saturation of hemoglobin, is approximately 28 mm Hg.

The relationship between partial pressure of oxygen and percent saturation of hemoglobin may be represented as a sigmoidal curve, the position of which is affected by pH (the Bohr effect). The higher the pH of the hemoglobin solution at a given partial pressure of oxygen, the greater the percent saturation with oxygen, and the lower the $P_{50}$; the oxygen saturation curve is shifted to the left on the abscissa. Conversely, the lower the pH of the hemoglobin solution, the lower the percent saturation with oxygen, and the higher $P_{50}$; the oxygen saturation curve is shifted to the right on the abscissa. Thus, as hemoglobin moves from the relatively alkaline pH of the lungs to the relatively acidic pH of oxygen-poor tissues (producing lactic acid by anaerobic respiration), the hemoglobin molecule will have a tendency to release its load of oxygen. Thus, in general, the affinity of hemoglobin for oxygen changes in the opposite direction as the $P_{50}$ of hemoglobin.

Modifications of the hemoglobin molecule or its conformation may be associated with changes in oxygen binding affinity. For example, association with 2,3-diphosphoglycerate (2,3-DPG, as occurs within the RBC) loosens the association between oxygen and hemoglobin, facilitating release of oxygen to tissues; serum levels of 2,3 DPG rise under physiologic conditions in which an increased delivery of oxygen is desirable, for example, at high altitudes and during pregnancy. Oxidation of the iron ion in the heme prosthetic group from Fe(II) to Fe(III) results in the formation of methemoglobin (met-Hb), which binds water so tightly as to preclude oxygen transfer. This oxidation or 'auto-oxidation' is an ongoing process in vivo which is maintained in check by a system of redox enzymes within the red blood cell.

Hemoglobin, the protein for oxygen transport and delivery, can be separated from the red blood cell wall membranes or stroma (stroma contain the specific antigens that determine blood type) and from other cell and plasma components. If such separation and isolation is effected, the resulting stroma-free hemoglobin contains no antigenic materials; thus, blood typing and matching are no longer necessary.

Stroma-free hemoglobin (SFH), taken out of the red blood cell microenvironment, has been found to exhibit a propensity to bind oxygen too tightly (a low $P_{50}$) and also to have a short circulating half-life following transfusion. The low $P_{50}$, reflective of a leftward shift in the hemoglobin oxygen binding curve, was, in part, a consequence of exposure of stroma-free hemoglobin to a higher pH in plasma (7.4) than that experienced within the erythrocyte (7.2); furthermore, the natural association between hemoglobin and 2,3-diphosphoglycerate was destroyed when hemoglobin was removed from the red cell, thus further lowering the $P_{50}$. In terms of clearance from the circulation, stroma-free hemoglobin is observed to be rapidly eliminated by the kidneys, with a transfusion half-life ($t_{1/2}$) of only about 100 minutes. The Hill coefficient for SFH is in the range of 2.3–2.8.

Chemically modified hemoglobins that address some of the shortcomings of stroma-free hemoglobin have been explored. Modifications described in the prior art include various means for intramolecular crosslinking of stroma-free hemoglobin; means for intermolecular crosslinking of stroma-free hemoglobin with low molecular weight agents; means for intra and inter molecular crosslinking of stroma-free hemoglobin with low molecular weight agents; and means for coupling stroma-free hemoglobin to other polymers.

Methods of intramolecular crosslinking of stroma-free hemoglobin are known in the art. See, for example, U.S. Pat. Nos. 4,584,130, 4,598,064 and 4,600,531. This treatment modifies stroma-free hemoglobin by covalently linking the lysine-99 residues on the alpha chains of the protein through a fumarate bridge. As a consequence of this intramolecular cross-linking, diaspirin crosslinked hemoglobin has an oxygen affinity equivalent to that of blood. Furthermore, diaspirin crosslinked hemoglobin (molecular weight 64,500) can no longer break down into dimers (molecular weight 32,250). As a result, the retention time of diaspirin alpha-alpha crosslinked hemoglobin is four to eight hours (which is two to four times that of stroma-free hemoglobin). However, this is not a sufficient length of time for utility in the treatment of acute hemorrhage, since an oxygen carrier is needed that can carry oxygen for several days when the patient has lost a considerable amount of blood. The $P_{50}$ of diaspirin crosslinked hemoglobin is in the physiological range (24–28 mm Hg) as is the Hill coefficient (2.5–2.8).

Hemoglobin molecules have also been intermolecularly crosslinked to each other through the use of low molecular weight crosslinking agents. For example, coupling of hemoglobin molecules to one another and/or to serum proteins and gelatin derivatives using dialdehydes, optimally followed by the addition of pyridoxal phosphate, is described in U.S. Pat. No. 4,336,248. Crosslinking with a bifunctional or polyfunctional, low molecular weight crosslinking agent has been described in U.S. Pat. Nos. 4,001,401, 4,001,200, 4,053,590 and 4,061,736. The products of intermolecular hemoglobin crosslinking are often not single soluble tetramers, but multiple tetramers of hemoglobin covalently linked to form soluble oligomers. Typically, products of such intermolecular crosslinking have oxygen-carrying and delivery properties that are not equivalent to blood ($P_{50}$ of 18–23 for glutaraldehyde-polymerized hemoglobin as compared to $P_{50}$ of 28 for whole blood) and Hill coefficients in the range 1.8–2.8). Furthermore, prior art products of intermolecular crosslinking by glutaraldehyde are known to be antigenic [see D. H. Marks et al., in Military Med. 152:473 (1987)].

In general, the intramolecular and intermolecular crosslinking of hemoglobin reduces some of the renal toxicity problems that result from the dissociation of unmodified hemoglobin into αβ-dimers. However, the colloidal osmotic pressure (COP) exerted by soluble hemoglobin is not significantly reduced by intramolecular crosslinking. This, therefore, limits the dosage level of soluble hemoglobin blood substitutes suitable for administration. In general, an increase in COP results in a decrease in hydrostatic pressure and a concomitant decrease in the glomerular filtration rate, resulting in oliguria and, in severe cases, anuria. The administration of soluble hemoglobins described in the prior art has resulted in bradycardia, a rise in blood pressure, and a fall in creatinine clearance. Vasoconstriction and tubular obstruction have been suggested as the cause of the renal effects, which are all linked to the use of soluble hemoglobins as blood substitutes. A highly polymerized form of hemoglobin, such as can be prepared as described herein, when used as a blood substitute, may alleviate these problems.

Highly fluorinated compounds, and particularly perfluorocarbon compounds, have also been considered as red blood cell substitutes, due to their high solubilities for oxygen. Among the highly fluorinated compounds useful for such applications are the perfluorocarbons, e.g., perfluorodecalin, perfluoroindane, perfluoromethyl adamantane, perfluorotripropyl amine, perfluorotributyl amine, perfluorooctyl bromide, and the like. For intravenous use, these fluorocarbons, being water-immiscible, must be dispersed as injectible emulsions. Emulsifiers typically used in these applications are egg yolk lecithin and egg phosphatides, both of which have the potential of precipitating allergic reactions. See, for example, PCT 92/06517, which describes an emulsion that contains a fluorochemical and phospholipids, such as lysophosphatidyl choline and lyophosphatidyl ethanolamine, as surfactants, or PCT 93/11868, which describes an emulsion with egg yolk lecithin as an emulsifier that contains highly fluorinated, chloro-substituted, non cyclic organic compounds as oxygen carriers.

Fluosol-DA (Alpha Therapeutics), an emulsion of perfluorodecalin and perfluorotripropyl amine, is the only FDA approved product for use in the prevention of transient ischemia in balloon coronary angioplasty. Another fluorocarbon product, Oxygent (Alliance Pharmaceuticals), or perfluorooctyl bromide, has approval as an oral imaging agent. For review of perfluoro compounds as blood substitutes, see Riess et al. in Angew Chem. Int. Ed. Engl. 17:621–634 (1978).

Blood substitutes described in the prior art contemplate only soluble hemoglobins as oxygen carriers. Indeed, it is conventionally accepted that an insoluble hemoglobin molecule (e.g., one that is excessively polymerized, or crosslinked with other hemoglobin molecules to the point of insolubility, or which is insoluble due to excessive denaturation, and the like) is not a candidate for reversible binding of oxygen, due to the high probability of destruction or disruption of the oxygen binding site within the molecule. In addition, the soluble hemoglobins of the prior art have Hill coefficients which are no greater than that of unmodified native hemoglobin.

In contrast, polymeric shells prepared from hemoglobin, as described herein, are 'giant' macroscopic molecules (due to extensive polymerization or crosslinking of large numbers of hemoglobin tetramer molecules) which, due to the large size thereof, is insoluble in aqueous medium. The polymerization occurs as a result of crosslinking of the sulfhydryl groups on the cysteine residues of the protein during the ultrasonic irradiation process. Polymeric shell prepared in accordance with the present invention typically comprises at least $10^4$ crosslinked polymer molecules, and may have as many as $10^{12}$ hemoglobin tetramers crosslinked into a single macroscopic 'megamer' of hemoglobin. It has unexpectedly been found that oxygen can bind reversibly to these insoluble constructs with affinities that are in the useful range for a red blood cell (RBC) substitute, i.e., $P_{50}$ between about 10 mm Hg to about 50 mm Hg.

Another surprising and unexpected observation concerning the insoluble hemoglobin construct (IHC) of the present invention is the surprisingly high Hill Coefficient (n) therefor. The Hill coefficient is a measure of the level of cooperativity between oxygen binding sites (heme units) within the hemoglobin tetrameric molecule. The maximum Hill coefficient for native hemoglobin is approximately 2.8, while Hill coefficients typically reported for prior art modified hemoglobins are less than 2.8. The measured Hill coefficients for the Insoluble Hemoglobin Constructs of the present invention are extraordinarily large, typically in the range of about 5 to about 25. Without wishing to be bound by any theory of action, these astonishingly high values can be attributed to the interaction or communication between the oxygen binding sites of the neighboring crosslinked tetrameric hemoglobin units. Essentially, it is believed that the large Hill coefficient is an indication that multiple tetramers cooperate in switching from the deoxy-T (tense) to the oxy-R (relaxed) state within the insoluble construct upon binding oxygen.

The unexpectedly large Hill coefficients observed in the hemoglobin constructs of the present invention have the advantage that the amount of oxygen carried per tetramer unit of hemoglobin far exceeds that achievable with native hemoglobin or modified hemoglobin of the prior art. This increased oxygen carrying capacity is greatly beneficial in the utility of the invention as a RBC substitute.

The hemoglobin constructs of the present invention achieve their maximum Hill coefficients at partial pressures of oxygen in the range of about 40–100 mm Hg. In other words, maximum cooperativity is achieved in this range of oxygen pressure. Since typical alveolar $pO_2$ lies within this range, maximum uptake of oxygen from the lungs by the hemoglobin constructs will be achieved when invention constructs are utilized as a blood substitute.

On the other hand, the release of oxygen to the tissues by the invention constructs is very similar to physiological hemoglobin, i.e., at typical tissue $pO_2$ (<40 mm Hg), most of the oxygen bound to the insoluble hemoglobin construct is released for oxygenation of the tissue. Thus, the crosslinked insoluble hemoglobin of the present invention has the unusual ability to bind oxygen at a higher capacity (due to large Hill coefficients) than prior art hemoglobin at typical loading pressures (such as in the lungs), while retaining the ability to release oxygen efficiently at typical pressures encountered in tissue.

Due to their crosslinked nature and size, the insoluble hemoglobin constructs of the present invention are likely to have an in vivo circulation time considerably longer than red blood cell (RBC) substitutes of the prior art. Furthermore, due to their large molecular (macroscopic) size, they are not likely to induce the renal toxicity problems that are commonplace with conventional tetrameric or oligomeric soluble forms of hemoglobin described in the prior art.

The hollow ('bubble-like' or microbubble) insoluble hemoglobin constructs of the present invention may be loaded with an appropriate gas within the hemoglobin shell or membrane. Thus when the hemoglobin 'microbubbles' are equilibriated with oxygen, e.g., in an external device or within the lungs, the central core of the construct or bubble is saturated with unbound or free oxygen that enters the core by molecular diffusion. Thus the constructs carry unbound molecular oxygen within their hollow core reservoir in addition to the oxygen bound to the hemoglobin forming the microbubble shell or membrane. The ability of this system to carry unbound (but entrapped) oxygen greatly increases the oxygen carrying capacity of the system over and above the oxygen carried by the hemoglobin alone. None of the prior art demonstrates this ability of carrying a reservoir of unbound molecular oxygen along with oxygen bound to hemoglobin.

Insoluble hemoglobin constructs can also be preloaded or saturated with oxygen prior to intravascular administration, for maximum oxygen delivery in short duration applications such as in coronary angioplasty or tumor therapy.

The discrete 'cellular' nature of insoluble hemoglobin constructs of the present invention renders them likely to transport oxygen in a physiologic manner, not unlike red blood cells in vivo. Due to the 'megameric' nature of invention insoluble hemoglobin constructs, they will have a colloidal osmotic pressure or oncotic pressure that is negligible compared to an equivalent amount (in terms of oxygen carrying capacity) of soluble hemoglobin of any of the prior art. This would allow for the intravenous infusion of high concentrations of invention hemoglobin constructs, while soluble hemoglobin of the prior art may be infused at a maximum concentration of only 6–8 g/dl for fear of severe water loss from tissues surrounding the vascular space due to osmotic gradients.

The invention lends itself to the use of other oxygen binding proteins as RBC substitutes. As an example, the protein myoglobin, which possesses a single oxygen binding heme group (but no crosslinkable cysteine residues) may be expected to behave in the same way. A genetically engineered myoglobin with at least two crosslinkable cysteine residues may be utilized to generate an insoluble myoglobin construct. A combination of oxygen binding proteins with proteins that have no affinity for oxygen may be utilized in formation of the insoluble constructs of the present invention, e.g., hemoglobin and albumin may be used.

The invention composition has a significant advantage over encapsulated hemoglobin compositions of the prior art. Liposomal hemoglobin formulations of the prior art comprise soluble hemoglobin within an external lipid layer. Liposome encapsulated hemoglobin compositions of the prior art suffer from several drawbacks that are overcome by the instant invention. Leakage of soluble hemoglobin from liposomal compositions can potentially cause nephrotoxicity. The insoluble constructs of the present invention will not leak soluble hemoglobin due to their extensively crosslinked nature. The aggregation of liposomes is known to activate the complement protein C3a. This aggregation is unlikely in the case of insoluble constructs due to their size which is considerably larger than the liposomal size range.

The invention composition of insoluble crosslinked hemoglobin avoids toxicity associated with soluble hemoglobin compositions of the prior art. Nephrotoxicity or renal toxicity of hemoglobin is mainly related to the clearance of soluble dimeric, tetrameric, or oligomeric hemoglobin from the circulation. The hemoglobin of the instant invention, being extensively crosslinked or 'megameric', cannot be cleared by the kidney and is unlikely to be nephrotoxic. The insoluble constructs of the instant invention cannot be cleared by the kidneys and therefore circumvent this problem. An additional advantage of the extensively crosslinked hemoglobin constructs of the present invention over the prior art is the increased intravascular persistence due to the insoluble form.

The morphology of the insoluble hemoglobin construct (IHC) was determined using transmission electron microscopy (TEM). To obtain the TEM micrograph of a cross-sectional slice of a bovine IHC, the IHC was fixed with glutaraldehyde, stained with osmium tetroxide and potassium ferrocyanate (to provide contrast in regions of high protein concentration), embedded in a low viscosity resin, and ultra-microtomed (slice thickness ~75 nm). Since some shrinkage in the overall diameter and some shape distortion of the IHC are expected during this process, the true diameter of the IHC is best represented by the solution particle size distribution (3 microns; std. dev. 1), rather than direct measurements from the TEM micrograph. A closer look at the TEM micrograph shows three distinctive regions: a clear central region; a dark, thin layer about the particle; and a loosely attached, diffuse, speckled gray region associated with the outer surface of the particle. The dark, thin layer is the IHC shell. It contains a high density of protein, and during staining procedure, develops the most contrast. The loosely attached, gray matter appears to be native protein that adheres to the IHC shell during the fixation step in the sample preparation. Initial measurements from this and many other micrographs indicate the shell thickness of the bovine hemoglobin IHC to be about 25–35 nm. Hemoglobin is a roughly spherical protein (L. Stryer, *Biochemistry*, W. H. Freeman, New York, 1988) with a diameter of 5.5 nm. Thus, the protein shell of the IHC is approximately 4 to 20 hemoglobin molecules (tetramers) thick. Thus, a 3.0 μm diameter bubble would contain about $10^4$ to $10^{12}$ hemoglobin molecules.

Examination of insoluble hemoglobin constructs (IHC) of the present invention (microbubbles or microspheres) by circular dichroism revealed that the content of alpha-helices and beta-pleated sheets in the IHC was not significantly different from that of purified stroma free hemoglobin (SFH). This observation is significant because it indicates that the crosslinking procedure and formation of insoluble hemoglobin does not result in denaturation (i.e., the alteration of the tertiary and quaternary structure) of the protein. This observation, of course, is corroborated by functional data showing the retention of reversible oxygen binding and cooperativity between oxygen binding heme units after the synthetic step.

The oxygen binding properties of the IHC have been determined. Since hemoglobin in the met-Fe(III) form cannot bind oxygen, the reduction system of Hyashi et al. (A. Hyashi, T. Suzuki, M. Shin. *Biochim. Biophys. Acta* 310:309, 1973) was used to reduce Fe(III) to Fe(II). The reduction system consists of various concentrations of glucose-6-phosphate, glucose-6-phosphate dehydrogenase, NADP, ferredoxin, ferredoxin reductase and catalase. Before each oxygen binding experiment, the reduction system was added to the IHC and remained at 4° C. for 24–36 hours.

A bovine and human hemoglobin IHC were synthesized as described in Example 14. As recognized by those of skill in the art, the hemoglobin employed can be derived from any vertebrate, invertebrate or eukaryotic source, or can be the product of genetic manipulation of vertebrate, invertebrate or eukaryotic cells. Table 1 provides a summary of the current results.

These oxygen binding data suggest that the IHC comprises substantially non-denatured hemoglobin. If it was denatured, no physiological (or less) reactivity would be observed.

Figure 2:
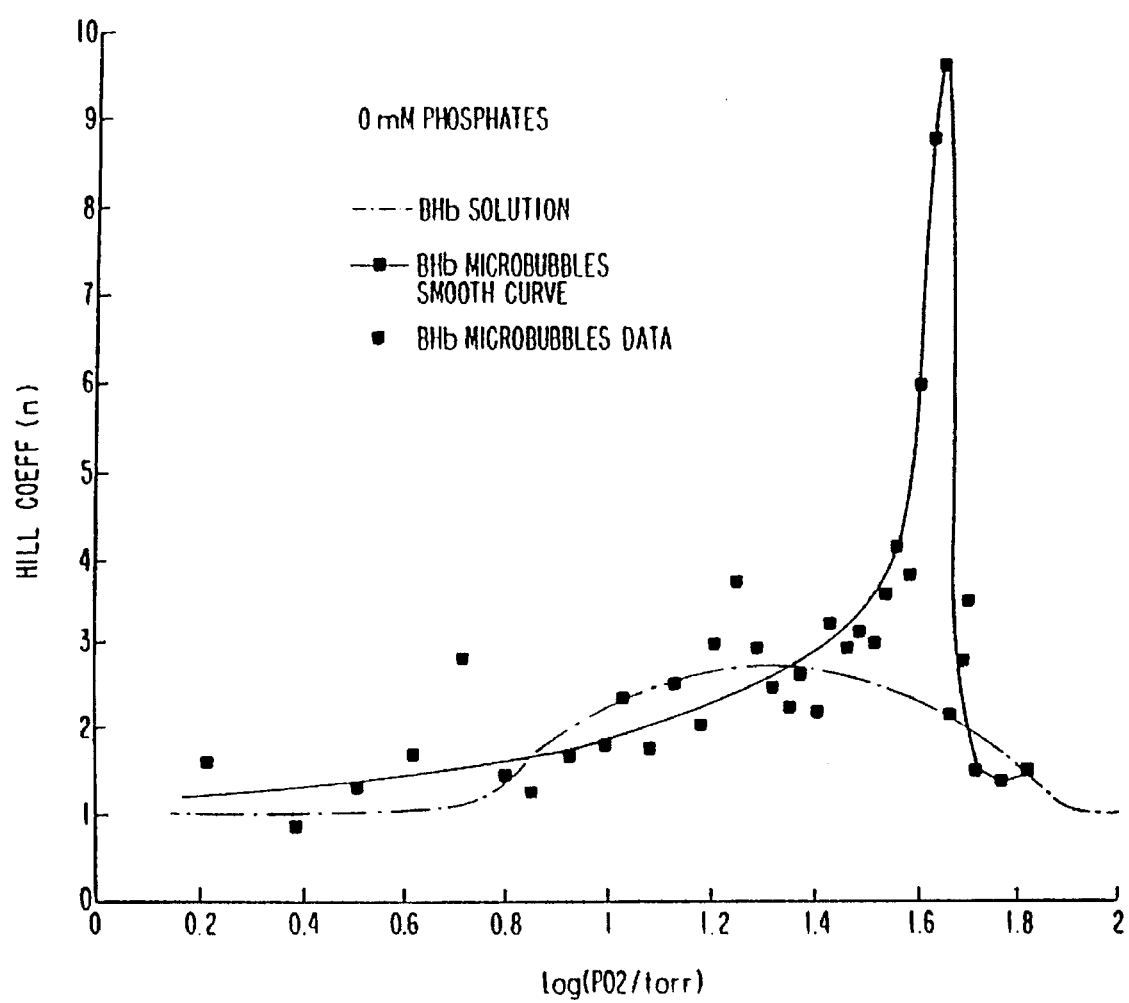

Oxygen binding curves for the reduced hemoglobin IHC and native stroma free hemoglobin in the absence of phosphates are sigmoidal in shape, indicating cooperativity in oxygen binding. The $P_{50}$ values (the pressure at which half of the available binding sites on hemoglobin are bound by oxygen) are similar in both curves (21 torr versus 22 torr). This result indicates that the IHC bind and release oxygen at similar oxygen pressures as native hemoglobin. Strikingly, the maximum Hill coefficient, $n_{max}$ (indicating the level of cooperativity between oxygen binding sites) of the IHC is significantly higher than the stroma-free hemoglobin solution (9.5 versus 2.6; see FIG. 2). Hill coefficients (n) were calculated using the formula:

$$\frac{\Delta \log(Y/1 - Y)}{\Delta \log P_{o2}}$$

where:
Y=fraction oxygenated, and
$P_{o2}$=oxygen partial pressure
Some smoothing was done by averaging each (delta) log (Y/1–Y) term over five consecutive points.

Figure 3:
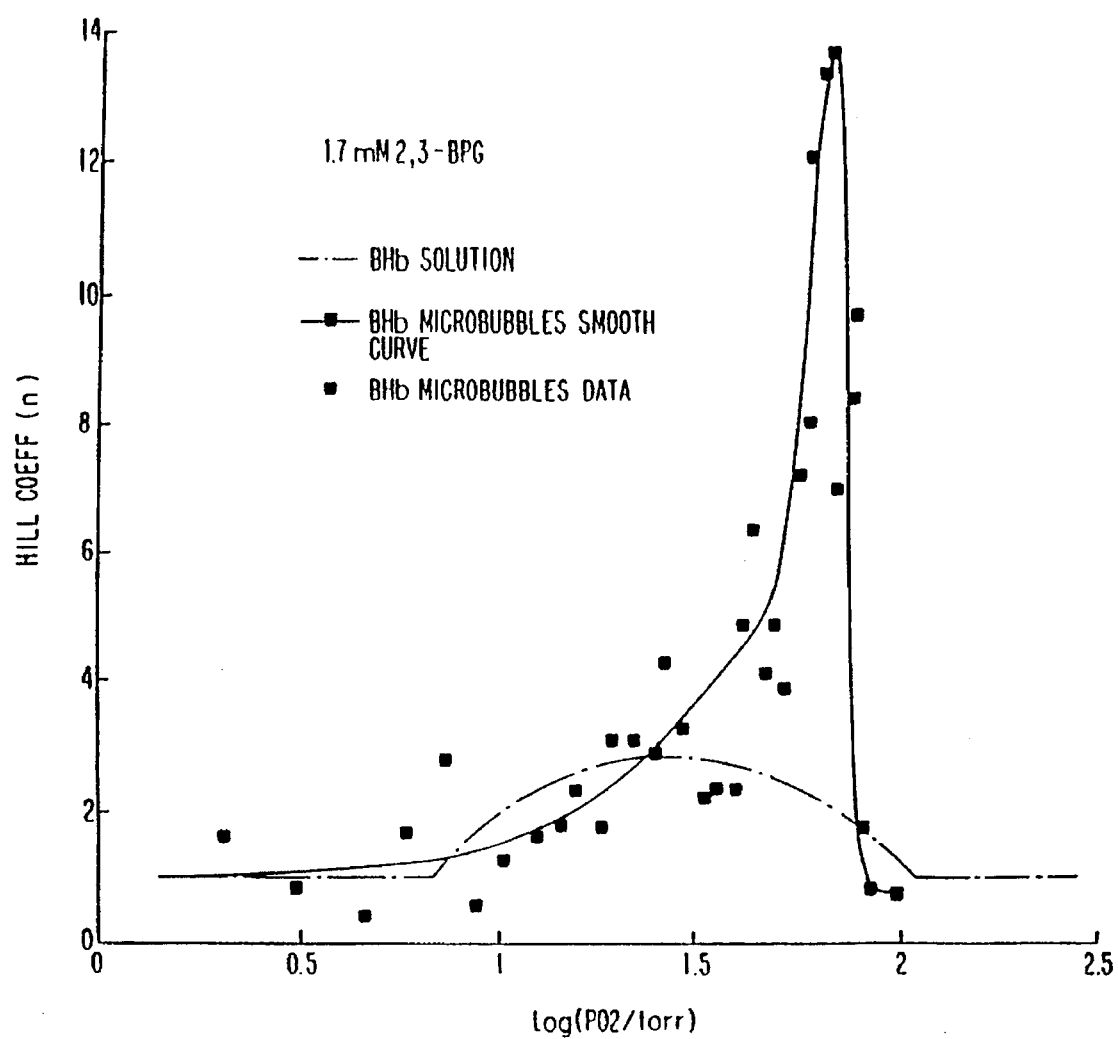

Allosteric effectors of native hemoglobin such as inositol hexaphosphate (IHP) and 2,3-bisphosphoglycerate (2,3-BPG) have been shown to increase both $P_{50}$ (i.e. lower oxygen affinity) and to enhance cooperativity. The same effects are seen in the IHC. Even though the $P_{50}$ values are increased by the same amount, a more dramatic effect is seen in the cooperativity of the IHC. The $n_{max}$ increased dramatically over that of native hemoglobin in the presence of 1.7 mM IHP (17.6 vs. 2.8) and 2,3-BPG (14 vs. 2.8) (see FIG. 3 and Table 1).

TABLE 1

Summary of $n_{max}$ and $P_{50}$ Values of Sonicated Hb Microbubbles and Unsonicated BHb in Various Concentrations of Phosphates

| Effector Concen. | Sonicated Hb Microbubbles | | | | Unsonicated Hb Solution | | | |
|---|---|---|---|---|---|---|---|---|
| | IHP | | 2,3-BPG | | IHP | | 2,3-BPG | |
| (mM) | $n_{max}$ | $P_{1/2}$ | $n_{max}$ | $P_{1/2}$ | $n_{max}$ | $P_{1/2}$ | $n_{max}$ | $P_{1/2}$ |
| 0 | 9.5 | 21.2 | 9.5 | 21.2 | 2.7 | 22.3 | 2.7 | 22.3 |
| 0.25 | 12.1 | 22.2 | 11.5 | 22.0 | 2.7 | 24.7 | 2.7 | 22.5 |
| 0.5 | 15.2 | 28.3 | 13.0 | 25.1 | 2.8 | 28.2 | 2.8 | 23.2 |
| 1.0 | 15.1 | 32.1 | 13.4 | 28.7 | 2.8 | 30.2 | 2.8 | 24.9 |
| 1.7 | 17.6 | 39.5 | 14.0 | 32.6 | 2.8 | 34.1 | 2.8 | 28.0 |

Note:
The Hill coefficients (n) for the BHb microbubbles are calculated from the formula:
$$n = \frac{\Delta \log(Y/1 - Y)}{\Delta \log P_{O_2}}$$
where Y is the fraction oxygenated and $P_{O2}$ is the oxygen pressure
For the microbubbles, each $\Delta$ log (Y/1 – Y) term is averaged over five consecutive points.

All binding experiments were done at 25° C. in Tris-buffer (pH 7.4). The IHC retain their ability to bind oxygen reversibly, as demonstrated by UV-visible spectra of the IHC, which indicates the presence of met-Fe(III), oxy-Fe(II) and deoxy-Fe(II) forms. The IHC can be cycled between the deoxy and oxy states for more than ten cycles without substantial degradation. This is important because it indicates that the environment surrounding the active heme site has not been altered significantly in the process of making the IHC red blood cell substitute.

This unexpectedly large increase in cooperativity apparently is due to the covalent bonding between hemoglobin tetramers within the IHC shell. The Hill coefficient cannot be greater than the number of interacting binding sites. The values of approximately 2.8 in native hemoglobin reflects the cooperativity in one tetramer. However, in the IHC shell, there is communication between several of the cross-linked tetramers (from the formation of disulfide bonds) upon binding oxygen. The interactions with nearest-neighbor tetramers are likely to be strongest; however, additional weaker interactions between tetramers further away may exist. Essentially, the large $n_{max}$ is an indication that multiple tetramers cooperate in switching from deoxy-T to the oxy-R state within the IHC shell upon binding oxygen. Again, TEM micrographs of hemoglobin IHC reveal a shell thickness of about six hemoglobin tetramers. A 3.0 μm diameter bubble would contain about $10^4$ to $10^{12}$ hemoglobin molecules.

Stability upon storage of the IHC was tested by particle counts at various time periods after preparation. The IHC were stored in sterile saline at 4° C. for up to 6 months. At 3 months, the concentration of the IHC had decreased by about 10%, while at 6 months the concentration had dropped by about 25–30%.

The auto-oxidation rate of the IHC (from oxy-Fe(II) to met-Fe(III)) has been determined to be greater than 60 hours, 96 hours, and 25 days at 37° C., 25° C. and 4° C., respectively. No special precautions were taken to maintain an inert atmosphere when these results were obtained. The prior art clearly demonstrates the benefit of maintaining an inert atmosphere such as nitrogen to decrease the rate of auto oxidation of hemoglobin. Storage under such conditions would be expected to greatly increase the fraction of Fe(II) hemoglobin maintained over a longer time period.

In addition, auto-oxidation may be prevented by storage of the IHC suspension with the reduction system of Hyashi et al. described above.

Pasteurization was investigated as a method of end stage sterilization for the IHC suspensions. Several different pasteurization conditions were utilized. Particle counts after each condition were used to determine any deleterious effects of temperature on the IHC.

Condition 1: Temperature of the IHC suspension was ramped from 25°–62.8° C. in 8 minutes and held at this temperature for 30 min. Particle counts showed a degradation of less than 20%.

Condition 2: Temperature of the IHC suspension was ramped from 25°–71.7° C. in 10 minutes and held at this temperature for 15 seconds. Particle counts showed a degradation of less than 20%.

Condition 3: Temperature of the IHC suspension was ramped from 25°–89.5° C. in 12 minutes and held at this temperature for 2 seconds. Particle counts showed a severe degradation of greater than 70%.

Thus, conditions 1 and 2 were found to be suitable as pasteurization modes. Gamma radiation as an end stage sterilization modality is also suitable.

The oxygen affinity (or $P_{50}$) of the IHC may altered by chemical modification of the hemoglobin with known allosteric effectors. In general, the modification of hemoglobin restricts the transition between the two oxy and deoxy conformations, so the oxygenation function is almost always altered in some way. For example if hemoglobin is modified in the oxy form, high oxygen affinity is usually favored, while the reverse is true if the modification is carried out in the deoxy condition. Derivatives of pyridoxal are useful modifiers since this molecule mimics the natural allosteric effector 2,3-diphosphoglycerate (DPG). They bind to the terminal amino groups of hemoglobin. For example the hemoglobin may be reacted with pyridoxal 5'-phosphate (PLP) that mimics the natural interaction of 2,3-DPG to increase the $P_{50}$. Other derivatives of pyridoxal such as 2-nor-2-formyl PLP, a bifunctional agent that links the hemoglobin β chains, or bis-pyridoxal tetraphosphate are useful modifiers. Other crosslinkers such as acyl tris(sodium methyl phosphates) may also be utilized to crosslink the β chains.

Aldehyde modifiers may also be used. For example glutaraldehyde is useful in polymerization of hemoglobin and can be used in conjunction with PLP.

Diaspirin esters such as 3,5-bis(dibromosalicyl)fumarate and the corresponding monoaspirin are useful allosteric modifiers. The aspirin binds between the a chains of hemoglobin and the monofunctional reagent to an internal lysine. Both increase the $P_{50}$ of hemoglobin.

Thus 'low affinity' or 'high affinity' constructs may be prepared for application in situations other than in cases of trauma and acute blood loss, such as in situations where local delivery of oxygen is required and beneficial.

A 'low affinity' construct, i.e., one with a high $P_{50}$ (>28 mm Hg), produced by the technique above has utility in the use of oxygen as an adjuvant in the treatment of tumors by radiation or chemotherapy. Such constructs are loaded to maximum oxygen capacity outside the body and then administered to the circulation of the tumor. This allows for a large amount of oxygen release at the tumor. Activated oxygen produced in the presence of radiation or chemotherapy results in greater cytotoxic activity at the tumor site.

A 'high affinity' construct ($P_{50}$<28 mm Hg) has utility for 'Ischemic Oxygen Delivery'. Ischemia, or oxygen deprivation of tissue may occur in a number of pathological conditions, e.g., stroke, myocardial infarction, and the like. The preferential release of oxygen in such areas would help minimize permanent tissue damage. An oxygen carrier or RBC substitute with oxygen affinity similar to whole blood will not preferentially release oxygen at such a site. However, one with a high oxygen affinity (i.e., a low $P_{50}$ compared to whole blood), while retaining most of its oxygen under conditions of normally encountered oxygen gradients, will preferentially release its oxygen at such an ischemic site due to the large oxygen gradient between the blood and tissue. The affinities of Insoluble hemoglobin constructs of the present invention may easily be manipulated to a suitable value ($P_{50}$) for such application by changing the nature of crosslinking, by using a suitable natural hemoglobin with the desired affinity, or by using a genetically engineered hemoglobin of suitable affinity.

The insoluble hemoglobin constructs of the present invention can encapsulate and thereby act as effective carriers of pharmacological agents such as oxygen carriers (e.g., fluorocarbons), drugs, diagnostic agents, and the like. The encapsulated fluorocarbons (FC) are effective oxygen carriers that transport and release dissolved oxygen in a linear relationship to the partial pressure of oxygen while the hemoglobin shell of the IHC transports and releases bound oxygen in a sigmoidal relationship to oxygen pressure. This unique combination of hemoglobin and fluorocarbon within the same formulation allows for maximal transport and release of oxygen in vivo.

The ability to deliver hemoglobin (Hb) and fluorocarbon (FC) simultaneously has not been disclosed in the prior art. Encapsulated fluorocarbon within the core of the hemoglobin shell is capable of acting as an oxygen reservoir. This combination allows for the delivery of oxygen bound to the carrier in a sigmoidal relationship with pressure (i.e., for hemoglobin) as well as linear relationship to pressure (i.e., for the fluorocarbon). This combination allows for the 'background' release of oxygen in a linear fashion (from fluorocarbon) with respect to tissue $pO_2$ and 'bolus' release of oxygen in a sigmoidal fashion (from hemoglobin) with respect to tissue $pO_2$. This allows for a more efficient oxygen delivery especially in cases where large amounts of oxygen are to be delivered for short periods, e.g., in tissue ischemia or tumor therapy.

The Hb/FC combination has the added advantage of external monitoring as to the localization of the intravascularly delivered dose. Since the $^{19}F$ nucleus is easily imaged by magnetic resonance imaging (MRI), it is possible to trace the accumulation of the delivered suspension within the vasculature and the tissue. This has great advantages in tumor treatment where oxygen is used as an adjuvant with radiation or chemotherapy to precisely monitor the delivery of the oxygen-carrying hemoglobin/FC suspension to the desired site.

A number of fluorocarbons (FCs) are suitable for use in the practice of the present invention, as described in detail below.

Furthermore, proteins that have no oxygen binding capabilities but have crosslinkable cysteine residues or sulfhydryl groups (native or artificially introduced) may be used to encapsulate biocompatible fluorocarbons with suitable oxygen affinities for use as blood substitutes. As an example, albumin can be used to encapsulate perfluorodecalin or perfluorotripropylamine for use as a blood substitute.

Several drugs are candidates for encapsulation in hemoglobin microspheres of the present invention. Several chemotherapeutic agents require the presence of oxygen for maximal tumor cytotoxicity. The delivery of such drugs within constructs of an oxygen carrier such as hemoglobin effectively combines the essential components of cytotoxicity into a single package. Several useful cytotoxic drugs are oil-soluble. These drugs may be dissolved in a fluorocarbon or other biocompatible oil such as soybean oil, safflower oil, coconut oil, olive oil, cotton seed oil, and the like. The oil/drug solution is subjected to ultrasonic irradiation with a hemoglobin solution to produce microspheres of oil/drug within a shell of crosslinked insoluble hemoglobin. The suspension may be oxygenated prior to intravascular administration. Oil-soluble cytotoxic drugs include cyclophosphamide, BCNU, melphalan, mitomycins, taxol and derivatives, taxotere and derivatives, camptothecin, adriamycin, etoposide, tamoxifen, vinblastine, vincristine and the like; nonsteroidal antiinflammatories such as ibuprofen, aspirin, piroxicam, cimetidine, and the like; steroids such as estrogen, prednisolone, cortisone, hydrocortisone, diflorasone, and the like, drugs such as phenesterine, mitotane, visadine, halonitrosoureas, anthrocyclines, ellipticine, diazepam, and the like; immunosuppressive agents such as cyclosporine, azathioprine, FK506, and the like.

Water-soluble drugs may also be encapsulated within the IHC shell by a method of double emulsion. First, an aqueous drug solution is emulsified with a biocompatible oil to obtain a water-in-oil (W/O) emulsion. The W/O emulsion is treated as an oil phase and subjected to ultrasonic irradiation with an aqueous hemoglobin solution as above to produce IHC containing within their shell, a microemulsion of the desired water-soluble drug. Emulsifiers contemplated for use in this embodiment of the present invention include the Pluronics (block copolymers of polyethylene oxide and polypropylene oxide), phospholipids of egg yolk origin (e.g., egg phosphatides, egg yolk lecithin, and the like); fatty acid esters (e.g., glycerol mono- and di-stearate, glycerol mono- and di-palmitate, and the like). Water-soluble drugs contemplated for use in this embodiment of the present invention include antineoplastic drugs such as actinomycin, bleomycin, cyclophosphamide, duanorubicin, doxorubicin, epirubicin, fluorouracil, carboplatin, cisplatin, interferons, interleukins, methotrexate, mitomycins, tamoxifen, estrogens, progestogens, and the like.

The double emulsion technique is also suitable for delivery of other aqueous-soluble material of therapeutic, diagnostic or nutritional value. For example, the hemoglobin content of the IHC may be increased by encapsulating a hemoglobin microemulsion into the IHC.

In order to make the IHC in a greater likeness to red blood cells, a phospholipid bilayer can be formed around the crosslinked hemoglobin microbubbles. Such a bilayer results in the formation of a true 'red cell analog' and may be created in a two step process. Charged phospholipids or lipids utilized in the formation of this bilayer include phosphatidyl choline, phosphatidyl ethanol amine, phosphatidyl serine, phosphatidyl inositol, phosphatidyl glycerol, sphingomyelin, dimyristoylphosphatidic acid, dipalmitoyl phosphatidic acid, sarcosinates (sarcosinamides), betaines, monomeric and dimeric alkyds, and the like. Nonionic lipids may also be utilized in this invention, including polyethylene fatty acid esters, polyethylene fatty acid ethers, diethanolamides, long chain acyl hexosamides, long chain acyl amino acid amides, long chain amino acid amines, polyoxyethylene sorbitan esters, polyoxy glycerol mono- and di-esters, glycerol mono- and di-stearate, glycerol mono- and di-oleate, glycerol mono- and di-palmitate, and the like.

Another variation on this technique is to utilize photopolymerizable lipids or lipids that may be readily crosslinked via a chemical reaction in order to provide a more stable lipid 'membrane' coat. Photopolymerizable lipids that may be utilized in the present invention include acrylate or methacrylate substituted lipids (such as phosphatidyl choline, phosphatidyl ethanol amine, phosphatidyl serine, phosphatidyl glycerol, dimyristoylphosphatidic acid, dipalmitoyl phosphatidic acid, and the like); lipids with native polymerizable unsaturation (such as unsaturated phosphatidyl cholines with diacetylene groups or conjugated diene groups, and the like), and so on. Lipids that readily undergo crosslinking via thiol-disulfide exchange also are good candidates for the formation of a stable lipid coat for the IHC. Examples of such lipids include derivatives of phosphatidyl cholines esterified with lipoic acid, and the like.

IHCs synthesized by ultrasonic irradiation can be administered as a suspension in a biocompatible medium, as described above, as well as other agents of nutritional value.

Preferred routes for in vivo administration are the intravenous, intraarterial, intramuscular, subcutaneous, intraperitoneal, oral, inhalational, topical, transdermal, suppository, pessary and the like.

In summary, the insoluble hemoglobin constructs of the present invention have numerous advantages over prior art soluble hemoglobin, prior art encapsulated soluble hemoglobin, and prior art fluorocarbon blood substitutes or oxygen carriers. These advantages include:

higher oxygen capacity;

variable oxygen affinity;

insoluble 'megameric' hemoglobin, which is expected to persist longer in circulation than prior art tetrameric or oligomeric soluble hemoglobin;

lower potential of kidney toxicity due to large molecular size;

less likely to leak hemoglobin than in the case of liposome encapsulated hemoglobin;

due to much larger size than liposomes, formation of aggregates that stimulate complement proteins is unlikely;

behaves more like RBC due to discrete 'cellular' nature compared to soluble hemoglobin of prior art;

can carry a reservoir of unbound oxygen along with oxygen bound to hemoglobin;

can be used as a fluorocarbon (FC) carrier without potentially allergic and toxic emulsifiers;

crosslinked hemoglobin in Hb/FC constructs provides for enhanced stability relative to prior art emulsified systems that use egg phosphatides and/or other synthetic surfactants;

release profiles of oxygen from Hb/FC is a combination of sigmoidal and linear in relation to tissue $pO_2$;

Hb/FC constructs can be detected and monitored in vivo by $^{19}F$ MRI;

hemoglobin or Hb/FC constructs may be used as drug carriers in addition to carrying oxygen;

a lipid bilayer membrane may be applied to the hemoglobin construct to make it appear more physiological;

the hemoglobin construct may be modified with polymers such as PEG to further increase intravascular persistence.

In accordance with yet another aspect of the present invention, it has been found that organofluorine-containing compounds, which in general are hydrophobic, water immiscible and consequently difficult to administer, can be entrapped in polymeric shells (as described above) for ease of delivery. Organofluorine-containing compounds entrapped within polymeric shells are readily usable and biocompatible. The particle size of polymeric shells produced in accordance with the present invention have an average diameter of approximately 2 microns, which is ideal for medical applications, since intravenous or intraarterial injections can be accomplished without risk of small blood vessel blockage and subsequent tissue damage (e.g., caused by ischemia due to oxygen depravation). For comparison, red blood cells are approximately 8 microns in diameter (thus injectable biomaterial should be smaller than 8–10 microns in diameter to prevent blood vessel blockage).

Naturally occurring fluorine atoms ($^{19}F$) give a clear nuclear magnetic resonance signal and thus can function as contrast agents or "probes" in MRI. The specific advantages for the use of $^{19}F$ include: 1) an extremely low native concentration in the body (fluorine is not naturally found in the body), 2) a high nuclear magnetic resonance sensitivity, 3) a magnetogyric ratio close to that of $^1H$, thus permitting $^{19}F$ magnetic resonance imaging to be carried out with only minor modifications of existing MRI devices, and 4) low toxicity of most organofluorine-containing compounds.

In general, fluorocarbons are non-toxic and biocompatible. Fluorocarbons are stable and unreactive, and consequently are not likely to be metabolized due to their strong carbon-fluorine bonds (approximately 130 kcal/mole). For comparison, carbon-hydrogen bonds (approximately 100 kcal/mole) are weaker and much more reactive. The FDA has approved two fluorocarbons, perfluorotripropyl amine and perfluorodecalin, for medicinal use as blood substitutes under the trade name of Fluosol DA.

A number of different fluorocarbons can be used in the practice of the present invention. For example, compounds satisfying the following generic formulae can be incorporated into polymeric shells employing the invention procedure as described herein:

(a) $C_xF_{2x+y-z}A_z$, wherein:
x=1–30, preferably 5–15,
y=2; or 0 or –2, when x≧2; or –4 when x≧4,
z=any whole number from 0 up to (2x+y–1), and
A is selected from H, halogens other than F, —CN, —OR, wherein R is H, alkyl, fluoroalkyl, alkenyl, fluoroalkenyl, fluoroalkynyl, aryl, alkynyl, fluoroaryl, alkanoyl, fluoroalkanoyl, alkenoyl, fluoroalkenoyl, alkynoyl, fluoroalkynoyl, (b) $[C_xF_{2x+y-z}A_z]_aJR_{b-a}$, wherein:
x, z, A and R are as defined above,
y'=+1; or –1 or –3, when x≧2; or –5 when x≧4,
J=O, S, N, P, Al, or Si,
a=1, 2, 3, or 4, and
b=2 for a divalent J, or 3 for a trivalent J, 4 for a tetravalent J, (c) A'—$[(CF_2)_x—O]_c$—A", wherein:
x is as defined above,
A' is selected from H, halogens, —CN, —OR, wherein R is H, alkyl, fluoroalkyl, alkenyl, fluoroalkenyl, alkynyl, fluoroalkynyl, aryl, fluoroaryl, alkanoyl, fluoroalkanoyl, alkenoyl, fluoroalkenoyl, alkynoyl, fluoroalkynoyl,
A" is selected from H or R, wherein R is as defined above,
c=1–200, preferably 2–50, or

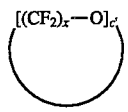
(d)

wherein:
x is as defined above, and
c'=2–20, preferably 2–8,
as well as mixtures of any two or more thereof.

Included within the above generic formulae are compounds having general formulae such as:

$C_xF_{2x}$, such as, for example, perfluoro-1-hexene ($C_6F_{12}$), perfluoro-2-hexene ($C_6F_{12}$), perfluoro-3-hexene ($C_6F_{12}$), and the like, cyclo-$C_xF_{2x}$, such as, for example, perfluorocyclohexane ($C_6F_{12}$), perfluorocyclooctane ($C_8F_{16}$), and the like, $C_xF_{2x-2}$, such as, for example, perfluoro-1-hexyne ($C_6F_{10}$), perfluoro-2-hexyne ($C_6F_{10}$), perfluoro-3-hexyne ($C_6F_{10}$), and the like, bicyclo-$C_xF_{2x-2}$, such as, for example, perfluorodecalin ($C_{10}F_{18}$), and the like, $C_xF_{2x+2}$, such as, for example, perfluorohexane ($C_6F_{14}$), perfluorooctane ($C_8F_{18}$), perfluorononane ($C_9F_{20}$), perfluorodecane ($C_{10}F_{22}$), perfluorododecane ($C_{12}F_{26}$), and the like, $C_xF_{2x-4}$, such as, for example, perfluoro-2,4-hexadiene, and the like, $C_xF_{2x+1}A$, such as, for example, perfluorotripropyl amine $[(C_3F_7)_3N]$, perfluorotributyl amine $[(C_4F_9)_3N]$, perfluoro-tert-tributyl amine, and the like, $C_xF_{2x-2}A_2$, such as, for example, $C_{10}F_{18}H_2$, and the like, as well as such highly fluorinated compounds as perfluoroindane, perfluoromethyl adamantane, perfluorooctyl bromide, perfluorodimethyl cyclooctane, perfluoro cyclooctyl bromide, perfluoro crown ethers, and the like.

Besides linear, branched-chain and cyclic fluorine-containing compounds as noted above, fluorinated crown ethers (such as, for example, perfluoro 12-crown-4, perfluoro 15-crown-5, perfluoro 18-crown-6, and the like) are also contemplated for use in the practice of the present invention.

In order to obtain good magnetic resonance images with high signal to noise ratios, it is advantageous to have a high number of equivalent fluorines. As used herein, the term "equivalent fluorines" refers to those fluorine substituents of a fluorine-containing compound which exist in a substantially similar micro-environment (i.e., substantially similar magnetic environment). Equivalent fluorines will produce one imaging signal. A high number of equivalent fluorines will produce a strong signal, undiluted by competing signals of "non-equivalent" fluorines.

As used herein, the term "non-equivalent fluorines" refers to those fluorine substituents of a fluorine-containing compound which exist in a substantially dis-similar microenvironment (i.e., substantially dis-similar magnetic environment), relative to other fluorine substituents on the same fluorine-containing compound. Thus, in contrast to equivalent fluorines, non-equivalent fluorines will give multiple signals due to their different chemical shifts. Thus, while compounds with a large number of non-equivalent fluorines are satisfactory for MRI applications, such compounds are not ideal for maximum imaging.

Of particular interest for application to vascular imaging are fluorocarbon-containing polymeric shells having prolonged circulation times. Currently used angiography techniques utilize X-ray contrast media and are invasive procedures. The potential of $^1$H-MRI has been recently demonstrated for angiography applications [Edelman & Warach, New England J. of Medicine 328:785–791 (1993)]. Similarly, $^{19}$F-MRI is useful for angiography, with a number of advantages, such as the ability to achieve high contrast with reference to surrounding tissue (which does not contain any native fluorine). Examples of applications of such methodology include the diagnosis and identification of intracranial aneurysms, arteriovenous malformations, occlusions of the superior vena cava, inferior vena cava, portal vein, pelvic vein, renal vein, renal mesenteric artery, peripheral mesenteric artery, and the like.

Fluorine-containing compounds entrapped in polymeric shells according to the present invention can be used for a variety of purposes, e.g., to obtain magnetic resonance images of various organs and/or tissues, to obtain oxygen profiles in organs and/or tissues, and also to measure local temperature. Invention contrast agents are not limited to use in MRI applications, but can also be used for such applications as ultrasonography and radiology. The other isotope of fluorine, $^{18}$F, can be used as a positron emission tomography (PET) contrast agent. Thus, with one fluorine-containing contrast agent, both PET and MRI diagnosis can be accomplished. Entrapment of other imaging agents, such as technetium and thallium compounds that are used in radiocontrast media, is also possible. Two examples of such contrast agents include Neurolyte and cardiolyte.

The use of invention compositions for oxygen detection is based upon the dramatic changes in NMR relaxation rate of $^{19}$F in the presence of a paramagnetic species such as oxygen. Since oxygen is paramagnetic, it will interact with the fluorine nucleus, increasing the relaxation rate of $^{19}$F from the excited state to the normal state. By monitoring this change in relaxation rate, it is possible to determine the oxygen concentration in a local area (by calibrating the MRI signal to a known concentration of oxygen).

The novelty of this system lies, for example, in 1) the use of MRI to obtain oxygen information, 2) the use of the oxygen paramagnetic influence on the $^{19}$F MRI (NMR) signal, 3) the use of polymeric shells to provide a constant and protective environment that is also permeable to oxygen, and the like.

By using fluorine-containing compounds that are solids which undergo a phase transition over physiological temperature ranges. (e.g., high molecular weight compounds, or combinations of fluorine-containing compounds), MRI can also be used to measure local temperature. Relaxation times are much longer in solids than in liquids, thus relaxation times will decrease dramatically as the transition temperature. (i.e., from solid to liquid) is reached. Dramatic changes are observed in the NMR spectrum during phase transition of solid to liquid. The shape of the MRI signal for a given fluorine-containing compound can be calibrated to a known temperature. By using a high molecular weight fluorine-containing compound within the polymeric shell (i.e., a fluorine-containing compound having a melting point of $\geq 15°$ C.), or by using a combination of fluorine-containing compound with non-fluorinated compound within the polymeric shell, the contents of the interior of the polymeric shell can be selected so as to provide a desired temperature range for phase transition to occur (typically in the range of about 22°–55° C.). The fluorocarbons within the shell will undergo a solid to liquid phase transition over the desired temperature range, altering substantially the observed relaxation rates, thus permitting in vivo temperature determination. Local temperature information would be especially useful, for example, in monitoring cancer patients during the hyperthermia treatment of cancer or in the detection of cancer cells (cancer cells are cooler than normal cells).

The fluorine-containing composition employed will determine the temperature range of the phase transition. Thus, this technique can be used over a wide temperature range, simply by changing the makeup of the fluorine-containing composition. For example, pure perfluoro-dodecane ($C_{12}F_{26}$) entrapped in a polymeric shell will undergo a solid to liquid phase transition at the melting point of the fluorocarbon (75° C.). However, this transition would be sharp and only a small amount of temperature information would be obtained. To obtain greater information, the melting point of the fluorine-containing composition can be spread over a wider range, for example, by simply adding another component to the pure fluorine-containing composition. It is well known in the art that a mixture will have a lower and broader melting point range than the corresponding pure components. Accordingly, for example, formulating perfluoro-dodecane with a lower molecular weight fluorocarbon will broaden the melting point range of the encapsulated composition. Similarly, a mixture of a fluorine-containing compound (e.g., perfluorododecane) with an alkane (e.g., pentane), for example, will broaden the melting point range of the entrapped composition.

In addition, chemically modified long chain fatty acids (e.g., heptadecanoic acid $[C_{17}H_{34}O_2]$, nonadecanoic acid $[C_{19}H_{38}O_2]$, and the like), alcohols (e.g., nonadecanol $[C_{19}H_{40}O]$, Docosanol $[C_{22}H_{46}O]$, and the like) to which fluorines can chemically be added can also be used in the practice of the present invention. For example, a dehydration coupling reaction between perfluoro-tert-butanol (t-$C_4F_9$—OH; PCR CHEMICALS) with any of the above-described reactive oxygen-containing compounds will produce a molecule that undergoes a solid to liquid phase transition and one that has nine equivalent fluorines. Similarly, a mixture of a fluorinated fatty acid and cholesterol, for example, will broaden the melting point range compared to the pure fluorinated fatty acid, thereby allowing for local temperature measurements to be made.

The novelty of this temperature detection system lies,. for example, 1) in the use of MRI to obtain spatially resolved temperature information, 2) in the use of the temperature dependence of the MRI (NMR) signal, 3) in the use of a fluorocarbon-containing composition that undergoes a solid to liquid phase transition in the desired temperature range, 4) in the use of the polymeric shell to provide a constant and protective environment for the medium, and 5) to obtain temperature information simultaneously with morphology information.

According to the present invention, particles of fluorine-containing composition are contained within a hell having a cross-sectional diameter of no greater than about 10 microns (as used herein, the term "micron" refers to a unit of measure of one one-thousandth of a millimeter). A cross-sectional diameter of less than 5 microns is more preferred, while a cross-sectional diameter of less than 1 micron is presently the most preferred for the intravenous route of administration.

Contrast agents of the present invention may be introduced into the body space in various ways depending on the imaging requirements. For example, aqueous liquid suspensions may be placed in the gastrointestinal tract by oral ingestion or suppository (e.g., to obtain images of the stomach and gastrointestinal tract), inserted by syringe into non-vascular spaces such as the cerebro-spinal cavity, or injected into the vascular system generally or into the vessels of a specific organ such as the coronary artery. In addition, contrast agents of the invention can also be injected into other body spaces such as the anterior and posterior eye spaces, the ear, the urinary bladder (e.g., by way of the urethra), the peritoneal cavities, ureter, urethra, renal pelvis, joint spaces of the bone, lymphatic vessels, the subarachnoid spaces, the ventricular cavities, and the like.

The polymeric shell containing solid or liquid cores of fluorine-containing composition allows for the directed delivery of high doses of the fluorine-containing composition agent in relatively small volumes. This minimizes patient discomfort at receiving large volumes of fluid.

In accordance with another embodiment of the present invention, there is provided an approach to the problem of administration of substantially water insoluble drugs such as taxol that has not been described in the literature. Thus, it has been discovered that delivery of such drugs can be accomplished as an aqueous suspension of micron size particles, or an aqueous suspension containing either particles of such drug or drug dissolved in a biocompatible non-aqueous liquid. This approach would facilitate the delivery of such drugs at relatively high concentrations, and thereby obviate the use of emulsifiers and their associated toxic side effects.

In accordance with yet another embodiment of the present invention, the above-described mode of administration is facilitated by novel drug-containing compositions wherein substantially water insoluble drug such as taxol is suspended in a biocompatible liquid, and wherein the resulting suspension contains particles of such drug (e.g., taxol) having a cross-sectional dimension no greater than about 10 microns. The desired particle size of less than about 10 microns can be achieved in a variety of ways, e.g., by grinding, spray drying, precipitation, ultrasonic irradiation, and the like.

Due to the crystal size of conventionally obtained substantially water insoluble drugs such as taxol, which is greater than 20 microns, solid particles of such drugs (e.g., taxol) have not been delivered in the form of a suspension in a vehicle such as normal saline. However, the present invention discloses the delivery of a particulate suspension of substantially water insoluble drugs (such as taxol) ground to a size less than about 10 microns, preferably less than about 5 microns and most preferably less than about 1 micron, which allows intravenous delivery in the form of a suspension without the risk of blockage in the microcirculation of organs and tissues.

Due to the microparticular nature of the delivered drug, most of it is cleared from the circulation 20 by organs having reticuloendothelial systems such as the spleen, liver, and lungs. This allows pharmacologically active agents in particulate form to be targeted to such sites within the body.

Biocompatible liquids contemplated for use in this embodiment are the same as those described above. In addition, parenteral nutritional agents such as Intralipid (trade name for a commercially available fat emulsion used as a parenteral nutrition agent; available from Kabi Vitrum, Inc., Clayton, N.C.), Nutralipid (trade name for a commercially available fat emulsion used as a parenteral nutrition agent; available from McGaw, Irvine, Calif.), Liposyn III (trade name for a commercially available fat emulsion used as a parenteral nutrition agent (containing 20% soybean oil, 1.2% egg phosphatides, and 2.5% glycerin); available from Abbott Laboratories, North Chicago, Ill.), and the like may be used as the carrier of the drug particles. Alternatively, if the biocompatible liquid contains a drug-solubilizing material such as soybean oil (e.g., as in the case of Intralipid), the drug may be partially or completely solubilized within the carrier liquid, aiding its delivery. An example of such a case is the delivery of taxol in Intralipid as the carrier. Presently preferred biocompatible liquids for use in this embodiment are parenteral nutrition agents, such as those described above.

In accordance with still another embodiment of the present invention, there is provided a composition for the in vivo delivery of taxol wherein taxol is dissolved in a parenteral nutrition agent.

The invention will now be described in greater detail by reference to the following non-limiting examples.

EXAMPLE 1

Preparation of Protein Shell Containing Oil

Three ml of a USP (United States Pharmacopoeia) 5% human serum albumin solution (Alpha Therapeutic Corporation) were taken in a cylindrical vessel that could be attached to a sonicating probe (Heat Systems, Model XL2020). The albumin solution was overlayered with 6.5 ml of USP grade soybean oil (soya oil). The tip of the sonicator probe was brought to the interface between the two solutions and the assembly was maintained in a cooling bath at 20° C. The system was allowed to equilibrate and the sonicator turned on for 30 seconds. Vigorous mixing occurred and a white milky suspension was obtained. The suspension was diluted 1:5 with normal saline. A particle counter (Particle Data Systems, Elzone, Model 280 PC) was utilized to determine size distribution and concentration of oil-containing protein shells. The resulting protein shells were determined to have a maximum cross-sectional dimension of about 1.35±0.73 microns, and the total concentration determined to be ~$10^9$ shells/ml in the original suspension.

As a control, the above components, absent the protein, did not form a stable miocroemulsion when subjected to ultrasonic irradiation. This result suggests that the protein is essential for formation of microspheres. This is confirmed by scanning electron micrograph and transmission electron micrograph studies as described below.

EXAMPLE 2

Parameters Affecting Polymeric Shell Formation

Several variables such as protein concentration, temperature, sonication time, concentration of pharmacologically active agent, and acoustic intensity were tested to optimize formation of polymeric shell. These parameters were determined for crosslinked bovine serum albumin shells containing toluene.

Polymeric shells made from solutions having protein concentrations of 1%, 2.5%, 5% and 10% were counted with the particle counter to determine a change in the size and number of polymeric shells produced. The size of the polymeric shells was found not to vary widely with protein concentration, but the number of polymeric shells per ml of "milky suspension" formed increased with the increase in concentration of the protein up to 5%. No significant change in the number of polymeric shells was found to occur above that concentration.

Initial vessel temperatures were found to be important for optimal preparation of polymeric shells. Typically, initial vessel temperatures were maintained between 0° C. and 45° C. The aqueous-oil interfacial tension of the oils used for formation of the polymeric shell was an important parameter, which also varied as a function of temperature. The concentration of pharmacologically active agent was found not to significantly effect the yield of protein shells. It is relatively unimportant if the pharmacologically active agent is incorporated in the dissolved state, or suspended in the dispersing medium.

Sonication time was an important factor determining the number of polymeric shells produced per ml. It was found that a sonication time greater than three minutes produced a decrease in the overall count of polymeric shells, indicating possible destruction of polymeric shells due to excessive sonication. Sonication times less than three minutes were found to produce adequate numbers of polymeric shells.

According to the nomograph provided by the manufacturer of the sonicator, the acoustic power rating of the sonicator employed herein is approximately 150 watts/$cm^2$. Three power settings in order of increasing power were used, and it was found that the maximum number of polymeric shells were produced at the highest power setting.

EXAMPLE 3

Preparation of Polymeric Shells Containing Dissolved Taxol

Taxol was dissolved in USP grade soybean oil at a concentration of 2 mg/ml. 3 ml of a USP 5% human serum albumin solution was taken in a cylindrical vessel that could be attached to a sonicating probe. The albumin solution was overlayered with 6.5 ml of soybean oil/taxol solution. The tip of the sonicator probe was brought to the interface between the two solutions and the assembly was maintained in equilibrium and the sonicator turned on for 30 seconds. Vigorous mixing occurred and a stable white milky suspension was obtained which contained protein-walled polymeric shells enclosing the oil/taxol solution.

In order to obtain a higher loading of drug into the crosslinked protein shell, a mutual solvent for the oil and the drug (in which the drug has a considerably higher solubility) can be mixed with the oil. Provided this solvent is relatively non-toxic (e.g., ethyl acetate), it may be injected along with the original carrier. In other cases, it may be removed by evaporation of the liquid under vacuum following preparation of the polymeric shells.

EXAMPLE 4

Stability of Polymeric Shells

Suspensions of polymeric shells at a known concentration were analyzed for stability at three different temperatures (i.e., 4° C., 25° C., and 38° C.). Stability was measured by the change in particle counts over time. Crosslinked protein (albumin) shells containing soybean oil (SBO) were prepared as described above (see Example 1), diluted in saline to a final oil concentration of 20% and stored at the above temperatures. Particle counts (Elzone) obtained for each of the samples as a function of time are summarized in Table 2.

TABLE 2

| | Protein Shells (#/ml · $10^{10}$) in saline | | |
|---|---|---|---|
| Day | 4° C. | 25° C. | 38° C. |
| 0 | 7.9 | 8.9 | 8.1 |
| 1 | 7.4 | 6.9 | 6.8 |
| 7 | 7.3 | 8.3 | 5.0 |
| 9 | 7.8 | 8.1 | 5.8 |
| 17 | 7.8 | 8.3 | 6.1 |
| 23 | 6.9 | 7.8 | 7.4 |
| 27 | 7.2 | 8.8 | 7.1 |

As demonstrated by the above data, the concentration of counted particles (i.e., polymeric shells) remains fairly constant over the duration of the experiment. The range is fairly constant and remains between about 7–9·$10^{10}$/ml, indicating good polymeric shell stability under a variety of temperature conditions over almost four weeks.

EXAMPLE 5

In Vivo Biodistribution—Crosslinked Protein Shells Containing a Fluorophore

To determine the uptake and biodistribution of liquid entrapped within protein polymeric shells after intravenous injection, a fluorescent dye (rubrene, available from Aldrich) was entrapped within a human serum albumin (HSA) protein polymeric shell and used as a marker. Thus, rubrene was dissolved in toluene, and crosslinked albumin shells containing toluene/rubrene were prepared as described above by ultrasonic irradiation. The resulting milky suspension was diluted five times in normal saline. Two ml of the diluted suspension was then injected into the tail vein of a rat over 10 minutes. One animal was sacrificed an hour after injection and another 24 hours after injection.

100 micron frozen sections of lung, liver, kidney, spleen, and bone marrow were examined under a fluorescent microscope for the presence of polymeric shell-entrapped fluorescent dye or released dye. At one hour, the majority of the polymeric shells appeared to be intact (i.e., appearing as brightly fluorescing particles of about 1 micron diameter), and located in the lungs and liver. At 24 hours, the dye was observed in the liver, lungs, spleen, and bone marrow. A general staining of the tissue was also observed, indicating that the shell wall of the polymeric shells had been digested, and the dye liberated from within. This result was consistent with expectations and demonstrates the potential use of invention compositions for delayed or controlled release of an entrapped pharmaceutical agent such as taxol.

EXAMPLE 6

Toxicity of Polymeric Shells Containing Soybean Oil (SBO)

Polymeric shells containing soybean oil were prepared as described in Example 1. The resulting suspension was diluted in normal saline to produce two different solutions, one containing 20% SBO and the other containing 30% SBO.

Intralipid, a commercially available TPN agent, contains 20% SBO. The $LD_{50}$ for Intralipid in mice is 120 ml/kg, or about 4 ml for a 30 g mouse, when injected at 1 cc/min.

Two groups of mice (three mice in each group; each mouse weighing about 30 g) were treated with invention composition containing SBO as follows. Each mouse was injected with 4 ml of the prepared suspension of SBO-containing polymeric shells. Each member of one group received the suspension containing 20% SBO, while each member of the other group received the suspension containing 30% SBO.

All three mice in the group receiving the suspension containing 20% SBO survived such treatment, and showed no gross toxicity in any tissues or organs when observed one week after SBO treatment. Only one of the three mice in the group receiving suspension containing 30% SBO died after injection. These results clearly demonstrate that oil contained within polymeric shells according to the present invention is not toxic at its $LD_{50}$ dose, as compared to a commercially available SBO formulation (Intralipid). This effect can be attributed to the slow release (i.e., controlled rate of becoming bioavailable) of the oil from within the polymeric shell. Such slow release prevents the attainment of a lethal dose of oil, in contrast to the high oil dosages attained with commercially available emulsions.

EXAMPLE 7

In vivo Bioavailability of Soybean Oil Released from Polymeric Shells

A test was performed to determine the slow or sustained release of polymeric shell-enclosed material following the injection of a suspension of polymeric shells into the blood stream of rats. Crosslinked protein (albumin) walled polymeric shells containing soybean oil (SBO) were prepared by sonication as described above. The resulting suspension of oil-containing polymeric shells was diluted in saline to a final suspension containing 20% oil. Five ml of this suspension was injected into the cannulated external jugular vein of rats over a 10 minute period. Blood was collected from these rats at several time points following the injection and the level of triglycerides (soybean oil is predominantly triglyceride) in the blood determined by routine analysis.

Five ml of a commercially available fat emulsion (Intralipid, an aqueous parenteral nutrition agent—containing 20% soybean oil, 1.2% egg yolk phospholipids, and 2.25% glycerin) was used as a control. The control utilizes egg phosphatide as an emulsifier to stabilize the emulsion. A comparison of serum levels of the triglycerides in the two cases would give a direct comparison of the bioavailability of the oil as a function of time. In addition to the suspension of polymeric shells containing 20% oil, five ml of a sample of oil-containing polymeric shells in saline at a final concentration of 30% oil was also injected. Two rats were used in each of the three groups. The blood levels of triglycerides in each case are tabulated in Table 3, given in units of mg/dl.

TABLE 3

| GROUP | SERUM TRIGLYCERIDES (mg/dl) | | | | | |
| --- | --- | --- | --- | --- | --- | --- |
| | Pre | 1 hr | 4 hr | 24 hr | 48 hr | 72 hr |
| Intralipid Control (20% SBO) | 11.4 | 941.9 | 382.9 | 15.0 | 8.8 | 23.8 |
| Polymeric Shells (20% SBO) | 24.8 | 46.7 | 43.8 | 29.3 | 24.2 | 43.4 |
| Polymeric Shells (30% SBO) | 33.4 | 56.1 | 134.5 | 83.2 | 34.3 | 33.9 |

Blood levels before injection are shown in the column marked 'Pre'. Clearly, for the Intralipid control, very high triglyceride levels are seen following injection. Triglyceride levels are then seen to take about 24 hours to come down to preinjection levels. Thus the oil is seen to be immediately available for metabolism following injection.

The suspension of oil-containing polymeric shells containing the same amount of total oil as Intralipid (20%) show a dramatically different availability of detectible triglyceride in the serum. The level rises to about twice its normal value and is maintained at this level for many hours, indicating a slow or sustained release of triglyceride into the blood at levels fairly close to normal. The group receiving oil-containing polymeric shells having 30% oil shows a higher level of triglycerides (concomitant with the higher administered dose) that falls to normal within 48 hours. once again, the blood levels of triglyceride do not rise astronomically in this group, compared to the control group receiving Intralipid. This again, indicates the slow and sustained availability of the oil from invention composition, which has the advantages of avoiding dangerously high blood levels of material contained within the polymeric shells and availability over an extended period at acceptable levels. Clearly, drugs delivered within polymeric shells of the present invention would achieve these same advantages.

Such a system of soybean oil-containing polymeric shells could be suspended in an aqueous solution of amino acids, essential electrolytes, vitamins, and sugars to form a total parenteral nutrition (TPN) agent. Such a TPN cannot be formulated from currently available fat emulsions (e.g., Intralipid) due to the instability of the emulsion in the presence of electrolytes.

EXAMPLE 8

Preparation of Crosslinked Protein-walled Polymeric Shells Containing a Solid Core of Pharmaceutically Active Agent Another method of delivering a poorly water-soluble drug such as taxol within a polymeric shell is to prepare a shell of polymeric material around a solid drug core. Such a 'protein coated' drug particle may be obtained as follows. The procedure described in Example 3 is repeated using an organic solvent to dissolve taxol at a relatively high concentration. Solvents generally used are organics such as benzene, toluene, hexane, ethyl ether, and the like. Polymeric shells are produced as described in Example 3. Five ml of the milky suspension of polymeric shells containing dissolved taxol are diluted to 10 ml in normal saline. This suspension is placed in a rotary evaporator at room temperature and the volatile organic removed by vacuum. After about 2 hours in the rotary evaporator, these polymeric shells are examined under a microscope to reveal opaque cores, indicating removal of substantially all organic solvent, and the presence of solid taxol within a shell of protein.

Alternatively, the polymeric shells with cores of organic solvent-containing dissolved drug are freeze-dried to obtain a dry crumbly powder that can be resuspended in saline (or other suitable liquid) at the time of use. In case of other drugs that may not be in the solid phase at room temperature, a liquid core polymeric shell is obtained. This method allows for the preparation of a crosslinked protein-walled shell containing undiluted drug within it. Particle size analysis shows these polymeric shells to be smaller than those containing oil. Although the presently preferred protein for use in the formation of the polymeric shell is albumin, other proteins such as α-2-macroglobulin, a known opsonin, could be used to enhance uptake of the polymeric shells by macrophage-like cells. Alternatively, a PEG-sulfhydryl (described below) could be added during formation of the polymeric shell to produce a polymeric shell with increased circulation time in vivo.

EXAMPLE 9

In vivo Circulation and Release Kinetics of Polymeric Shells

Solid core polymeric shells containing taxol were prepared as described above (see, for example, Example 3) and suspended in normal saline. The concentration of taxol in the suspension was measured by HPLC as follows. First, the taxol within the polymeric shell was liberated by the addition of 0.1M mercaptoethanol (resulting in exchange of protein disulfide crosslinkages, and breakdown of the crosslinking of the polymeric shell), then the liberated taxol was extracted from the suspension with acetonitrile. The resulting mixture was centrifuged and the supernatant freeze-dried. The lyophilate was dissolved in methanol and injected onto an HPLC to determine the concentration of taxol in the suspension. The taxol concentration was found to be about 1.6 mg/ml.

Rats were injected with 2 ml of this suspension through a jugular catheter. The animal was sacrificed at two hours, and the amount of taxol present in the liver determined by HPLC. This required homogenization of the liver, followed by extraction with acetonitrile and lyophilization of the supernatant following centrifugation. The lyophilate was dissolved in methanol and injected onto an HPLC. Approximately 15% of the administered dose of taxol was recovered from the liver at two hours, indicating a significant dosage to the liver. This result is consistent with the known function of the reticuloendothelial system of the liver in clearing small particles from the blood.

EXAMPLE 10

Preparation of Crosslinked PEG-walled Polymeric Shells

As an alternative to the use of thiol (sulfhydryl) containing proteins in the formation of, or as an additive to polymeric shells of the invention, a thiol-containing PEG was prepared. PEG is known to be nontoxic, noninflammatory, nonadhesive to cells, and in general biologically inert. It has been bound to proteins to reduce their antigenicity and to liposome forming lipids to increase their circulation time in vivo. Thus incorporation of PEG into an essentially protein shell would be expected to increase circulation time as well as stability of the polymeric shell. By varying the concentration of PEG-thiol added to the 5% albumin solution, it was possible to obtain polymeric shells with varying stabilities in vivo. PEG-thiol was prepared by techniques available in the literature (such as the technique of Harris and Herati, as described in Polymer Preprints Vol. 32:154–155 (1991)).

PEG-thiol of molecular weight 2000 g/mol was dissolved at a concentration of 1% (0.1 g added to 10 ml) in a 5% albumin solution. This protein/PEG solution was overlayered with oil as described in Example 1 and sonicated to produce oil-containing polymeric shells with walls comprising crosslinked protein and PEG. These polymeric shells were tested for stability as described in Example 4.

Other synthetic water-soluble polymers that may be modified with thiol groups and utilized in lieu of PEG include, for example, polyvinyl alcohol, polyhydroxyethyl methacrylate, polyacrylic acid, polyethyloxazoline, polyacrylamide, polyvinyl pyrrolidinone, polysaccharides (such as chitosan, alginates, hyaluronic acid, dextrans, starch, pectin, and the like), and the like.

For example, fluorocarbon-containing protein shells having prolonged circulation times in vivo were found to have particular benefit for imaging the vascular system. These shells remained within the circulation for extended periods, relative to shells not containing PEG in the shell walls. This allowed, for example, visulation of cardiac circulation, and provided a non-invasive means of evaluating the coronary circulation, instead of using conventional invasive techniques such as angiography.

EXAMPLE 11

Targeting of Immunosuppressive Agent to Transplanted Organs using Intravenous Delivery of Polymeric Shells Containing Such Agents Immunosuppressive agents are extensively used following organ transplantation for the prevention of rejection episodes. In particular, cyclosporine, a potent immunosuppressive agent, prolongs the survival of allogeneic transplants involving skin, heart, kidney, pancreas, bone marrow, small intestine, and lung in animals. Cyclosporine has been demonstrated to suppress some humoral immunity and to a greater extent, cell mediated reactions such as allograft rejection, delayed hypersensitivity, experimental allergic encephalomyelitis, Freund's adjuvant arthritis, and graft versus host disease in many animal species for a variety of organs. Successful kidney, liver and heart allogeneic transplants have been performed in humans using cyclosporine.

Cyclosporine is currently delivered in oral form either as capsules containing a solution of cyclosporine in alcohol, and oils such as corn oil, polyoxyethylated glycerides and the like, or as a solution in olive oil, polyoxyethylated glycerides, and the like. It is also administered by intravenous injection, in which case it is dissolved in a solution of ethanol (approximately 30%) and Cremaphor (polyoxyethylated castor oil) which must be diluted 1:20 to 1:100 in normal saline or 5% dextrose prior to injection. Compared to an intravenous (i.v.) infusion, the absolute bioavailibility of the oral solution is approximately 30% (Sandoz Pharmaceutical Corporation, Publication SDI-Z10 (A4), 1990). In general, the i.v. delivery of cyclosporine suffers from similar problems as the currently practiced i.v. delivery of taxol, i.e., anaphylactic and allergic reactions believed to be due to the Cremaphor, the delivery vehicle employed for the i.v. formulation. In addition, the intravenous delivery of drug (e.g., cyclosporike) encapsulated as described here avoids dangerous peak blood levels immediately following administration of drug. For example, a comparison of currently available formulations for cyclosporine with the above-described encapsulated form of cyclosporine showed a five-fold decrease in peak blood levels of cyclosporine immediately following injection.

In order to avoid problems associated with the Cremaphor, cyclosporine contained within polymeric shells as described above may be delivered by i.v. injection. It may be dissolved in a biocompatible oil or a number of other solvents following which it may be dispersed into polymeric shells by sonication as described above. In addition, an important advantage to delivering cyclosporine (or other immunosuppressive agent) in polymeric shells has the advantage of local targeting due to uptake of the injected material by the RES system in the liver. This may, to some extent, avoid systemic toxicity and reduce effective dosages due to local targeting. The effectiveness of delivery and targeting to the liver of taxol contained within polymeric shells following intravenous injection is demonstrated in Example 9. A similar result would be expected for the delivery of cyclosporine (or other putative immunosuppressive agent) in accordance with the present invention.

EXAMPLE 12

Antibody Targeting of Polymeric Shells

The nature of the polymeric shells of the invention allows for the attachment of monoclonal or polyclonal antibodies to the polymeric shell, or the incorporation of antibodies into the polymeric shell. Antibodies can be incorporated into the polymeric shell as the polymeric microcapsule shell is being formed, or antibodies can be attached to the polymeric microcapsule shell after preparation thereof. Standard protein immobilization techniques can be used for this purpose. For example, with protein microcapsules prepared from a protein such as albumin, a large number of amino groups on the albumin lysine residues are available for attachment of suitably modified antibodies. As an example, antitumor agents can be delivered to a tumor by incorporating antibodies against the tumor into the polymeric shell as it is being formed, or antibodies against the tumor can be attached to the polymeric microcapsule shell after preparation thereof. As another example, gene products can be delivered to specific cells (e.g., hepatocytes or certain stem cells in the bone marrow) by incorporating antibodies against receptors on the target cells into the polymeric shell as it is being formed, or antibodies against receptors on the target cells can be attached to the polymeric microcapsule shell after preparation thereof. In addition, monoclonal antibodies against nuclear receptors can be used to target the encapsulated product to the nucleus of certain cell types.

EXAMPLE 13

Polymeric Shells as Carriers for Polynucleotide Constructs, Enzymes and Vaccines As gene therapy becomes more widely accepted as a viable therapeutic option (at the present time, over 40 human gene transfer proposals have been approved by NIH and/or FDA review boards), one of the barriers to overcome in implementing this therapeutic approach is the reluctance to use viral vectors for the incorporation of genetic material into the genome of a human cell. Viruses are inherently toxic. Thus, the risks entailed in the use of viral vectors in gene therapy, especially for the treatment of non-lethal, non-genetic diseases, are unacceptable. Unfortunately, plasmids transferred without the use of a vital vector are usually not incorporated into the genome of the target cell. In addition, as with conventional drugs, such plasmids have a finite half life in the body. Thus, a general limitation to the implementation of gene therapy (as well as antisense therapy, which is a reverse form of gene therapy, where a nucleic acid or oligonucleotide is introduced to inhibit gene expression) has been the inability to effectively deliver nucleic acids or oligonucleotides which are too large to permeate the cell membrane.

The encapsulation of DNA, RNA, plasmids, oligonucleotides, enzymes, and the like, into protein microcapsule shells as described herein can facilitate their targeted delivery to the liver, lung, spleen, lymph and bone marrow. Thus, in accordance with the present invention, such biologics can be delivered to intracellular locations without the attendant risk associated with the use of viral vectors. This type of formulation facilitates the non-specific uptake or endocytosis of the polymeric shells directly from the blood stream to the cells of the RES, into muscle cells by intramuscular injection, or by direct injection into tumors. In addition, monoclonal antibodies against nuclear receptors can be used to target the encapsulated product to the nucleus of certain cell types.

Diseases that can be targeted by such constructs include diabetes, hepatitis, hemophilia, cystic fibrosis, multiple sclerosis, cancers in general, flu, AIDS, and the like. For example, the gene for insulin-like growth factor (IGF-1) can be encapsulated into protein microcapsule shells for delivery for the treatment of diabetic peripheral neuropathy and cachexia. Genes encoding Factor IX and Factor VIII (useful for the treatment of hemophilia) can be targeted to the liver by encapsulation into protein microcapsule shells of the present invention. Similarly, the gene for the low density lipoprotein (LDL) receptor can be targeted to the liver for treatment of atherosclerosis by encapsulation into protein microcapsule shells of the present invention.

Other genes useful in the practice of the present invention are genes which re-stimulate the body's immune response against cancer cells. For example, antigens such as HLA-B7, encoded by DNA contained in a plasmid, can be incorporated into a protein microcapsule shell of the present invention for injection directly into a tumor (such as a skin cancer). Once in the tumor, the antigen will recruit to the tumor specific cells which elevate the level of cytokines (e.g., IL-2) that render the tumor a target for immune system attack.

As another example, plasmids containing portions of the adeno-associated virus genome are contemplated for encapsulation into protein microcapsule shells of the present invention. In addition, protein microcapsule shells of the present invention can be used to deliver therapeutic genes to CD8+ T cells, for adoptive immunotherapy against a variety of tumors and infectious diseases.

Protein microcapsule shells of the present invention can also be used as a delivery system to fight infectious diseases via the targeted delivery of an antisense nucleotide, for example, against the hepatitis B virus. An example of such an antisense oligonucleotide is a 21-mer phosphorothioate against the polyadenylation signal of the hepatitis B virus.

Protein microcapsule shells of the present invention can also be used for the delivery of the cystic fibrosis transmembrane regulator (CFTR) gene. Humans lacking this gene develop cystic fibrosis, which can be treated by nebulizing protein microcapsule shells of the present invention containing the CFTR gene, and inhaling directly into the lungs.

Enzymes can also be delivered using the protein microcapsule shells of the present invention. For example, the enzyme, DNAse, can be encapsulated and delivered to the lung. Similarly, ribozymes can be encapsulated and targeted to virus envelop proteins or virus infected cells by attaching suitable antibodies to the exterior of the polymeric shell. Vaccines can also be encapsulated into polymeric microcapsules of the present invention and used for subcutaneous, intramuscular or intravenous delivery.

EXAMPLE 14

Preparation of Insoluble Hemoglobin Constructs (IHC) for use as a Red Blood Cell Substitute A 20 ml glass reaction cell, titanium horn and collar were washed with alcohol and sterile saline prior to synthesis as was all equipment used. In a typical reaction, 3.5 ml of 5% w/v hemoglobin (human or bovine) was added to a reaction cell which was attached to the ultrasonic horn (Heat Systems XL2020, 20 KHz, 400 W maximum power). The horn and cell were then submerged in a temperature control bath set to 55° C. Reactions run at 55° C. appeared to be optimum, however product can be synthesized over a wide range of temperatures (0° to 80° C.). The pH was 6.8. Temperature control is critical to high yields of material, and the optimum temperature depends on the specific experimental configuration. The ultrasonic source turned on at a power setting of 7. Using the manufacturer's nomograph suggested a power output of approximately 150 W/cm$^2$. The reaction is complete in about 30 seconds. Yields at shorter and longer reaction times appear to be less. For bovine hemoglobin, the 2.5% w/v solution was passed through a Sephadex G-25 gel permeation column to remove any anions such as phosphates. In a typical synthesis of human hemoglobin IHC, the ultrasonic horn was positioned at the air-water interface. The homogeneous suspension produced contains proteinaceous red blood cells. The aqueous suspension may then be stored in a sterile container at 4° C.

A typical reaction yields a solution that contains approximately $3 \times 10^8$ IHC shells per ml with an average shell diameter of 3 microns with a standard deviation of 1 micron. This synthetic procedure yields high concentrations of micron-sized biomaterial with narrow size distributions.

After the synthesis, the IHC remain as a suspension in the native protein solution. To separate the IHC from the unreacted protein, several methods were used: filtration, centrifugation and dialysis. The first method included filtering the mixture through an Anotop syringe filter with 0.2 μm diameter pore size (Whatman, Inc.). The filter was washed with several volumes of water until the filtrate contained very little or no protein (as determined by UV-Visible spectroscopy). The IHC were "backwashed" out of the filter and resuspended in an equivalent volume of saline. The second purification procedure involved the use of a Centricon centrifuge filter with a molecular-weight cut-off of 100 kilodaltons (kD). The centrifuge filter is a centrifuge tube separated by a filtration membrane in the middle. Centrifugation of the IHC solution at 1000 G for 5 minutes allowed most of the unreacted hemoglobin (64.5 kD) to pass through the membrane. Finally, dialysis with a large molecular weight (300 kD) membrane was also used to purify the IHC. However, this method required approximately 2 days of dialysis. The preferred method for the purification of the IHC is with the Centricon centrifugation.

EXAMPLE 15

Preparation of an Insoluble Hemoglobin/Albumin Construct (IHAC) as a Red Blood Cell Substitute A 20 ml glass reaction cell, titanium horn and collar were washed with alcohol and sterile saline prior to synthesis as was all equipment used. In a typical reaction, 3.5 ml of a 5% w/v hemoglobin and albumin (human or bovine; hemoglobin/albumin ratio varied from 0.5 to 2) was added to a reaction cell which was attached to the ultrasonic horn (Heat Systems XL2020, 20 KHz, 400 W maximum power). The horn and cell were then submerged in a temperature control bath set to 55° C. Reactions run at 55° C. appeared to be optimum, however product can be synthesized over a wide range of temperatures (0° to 80° C.). The pH was 6.8. Temperature control is critical to high yields of material, and the optimum temperature depends on the specific experimental configuration. The ultrasonic source turned on at a power setting of 7. Using the manufacturer's nomograph suggested a power output of approximately 150 W/cm$^2$. The reaction is complete in about 30 seconds. Yields at shorter and longer reaction times appear to be less. The homogeneous suspension produced contains the proteinaceous red blood cell substitute. The aqueous suspension was filtered, washed, resuspended in sterile buffered saline and stored in a sterile container at 4° C.

Again as described above, typical reaction yields a solution that contains roughly $10^8$ shells per ml with an average shell diameter of 3 microns with a standard deviation of 1 micron. This synthetic procedure yields high concentrations of micron-sized biomaterial with narrow size distributions.

Alternately a flow-through system that allows the continuous processing of the IHC can be utilized. Such a system consists of peristaltic pumps that continously pump streams of hemoglobin and optionally a biocompatible oil or fluorocarbon into a reaction vessel with a sonicator probe. A suitable residence time is maintained in the vessel and the IHC recovered by overflow from the vessel into a recovery tank. The unreacted hemoglobin solution is recycled into the reaction vessel.

EXAMPLE 16

Preparation of Insoluble Hemoglobin Constructs Containing Encapsulated Fluorocarbons A 20 ml glass reaction cell, titanium horn and collar were washed with alcohol and sterile saline prior to synthesis as was all equipment used. In a typical reaction, 3.5 ml of a 5% w/v hemoglobin (human or bovine) was added to a reaction cell which was attached to the ultrasonic horn (Heat Systems XL2020, 20 KHz, 400 W maximum power). A fluorocarbon, perfluorodecalin 3.5 ml, was added to the reaction vessel. The horn and cell were then submerged in a temperature control bath set to 20° C. The pH of the aqueous phase was 6.8. The ultrasonic source turned on at a power setting of 7. Using the manufacturer's nomograph suggested a power output of approximately 150 W/cm$^2$. The reaction is complete in about 30 seconds. The homogeneous suspension produced contains the microcapsules or microspheres of crosslinked insoluble hemoglobin shells with encapsulated perfluorodecalin in the interior. The milky suspension is filtered, washed, resuspended in sterile buffered saline as above and stored in a sterile container at 4° C.

Again as described above, typical reaction yields a solution that contains roughly $10^8$ shells per ml with an average shell diameter of 3 microns with a standard deviation of 1 micron. This synthetic procedure yields high concentrations of micron-sized biomaterial with narrow size distributions.

EXAMPLE 17

Preparation of Insoluble Albumin Constructs Containing Encapsulated Fluorocarbons A 20 ml glass reaction cell, titanium horn and collar were washed with alcohol and sterile saline prior to synthesis as was all equipment used. In a typical reaction, 3.5 ml of a 5% w/v albumin (human or bovine) was added to a reaction cell which was attached to the ultrasonic horn (Heat Systems XL2020, 20 KHz, 400 W maximum power). A fluorocarbon, perfluorodecalin (or perfluorotripropyl amine) 3.5 ml, was added to the reaction vessel. The horn and cell were then submerged in a temperature control bath set to 20° C. The pH of the aqueous phase was 6.8. The ultrasonic source turned on at a power setting of 7. Using the manufacturer's nomograph suggested a power output of approximately 150 W/cm$^2$. The reaction is complete in about 30 seconds. The homogeneous suspension produced contains the microcapsules or microspheres of crosslinked insoluble Albumin shells with encapsulated perfluorodecalin (or perfluorotripropyl amine) in the interior. The milky suspension is filtered, washed, resuspended in sterile buffered saline as above and stored in a sterile container at 4° C.

Again as described above, typical reaction yields a solution that contains roughly 10$^8$ shells per ml with an average shell diameter of 3 microns with a standard deviation of 1 micron. This synthetic procedure yields high concentrations of micron-sized biomaterial with narrow size distributions.

EXAMPLE 18

Insoluble Hemoglobin Constructs further Modified with Allosteric Modifiers such as Pyridoxal 5'-Phosphate In order to obtain hemoglobin constructs with variable affinities to oxygen (i.e., variable P$_{50}$), the IHC were further reacted with PLP, a known allosteric modulator. A suspension of IHC (obtained as in Example 14) in tris buffer was deoxygenated at 10C under nitrogen. 10 ml of the deoxygenated IHC suspension was taken in each of six separate reaction vessels. Different molar ratios of PLP/Hb were added to each of the vessels. They were 0.1/3/0, 0.75/3.0, 1.5/3.0, 3.0/3.0, 4.2/3.0, 6.0/3.0. After 30 minutes, a tenfold excess of sodium borohydride is added an allowed to reduce the Schiff's base for another 30 minutes. The suspension is then filtered by centrifugation, backwashed 3 times with buffered saline, resuspended in buffered saline and stored at 4° C. This modification targets the amino terminal groups of the b-globin chain in deoxyhemoglobin. In this respect the modification closely mimics the action of 2,3-DPG (which binds at lysine EF6(82)b) in stabilizing the deoxy confirmation.

The six different degrees of modification will result in IHC with increasing P$_{50}$ (decreasing oxygen affinities) with increasing degree of PLP substitution.

EXAMPLE 19

Insoluble Constructs with Crosslinked Shells of Hemoglobin and Polyethylene Glycol Polyethylene glycol (PEG) is known to be nontoxic, noninflammatory, nonadhesive to cells, and in general biologically inert. Proteins that are attached with PEG have been found to be less antigenic. With liposomes, circulation was found increased upon binding/incorporation of PEG. Thus incorporation of PEG into the RBC will be expected to increase circulation time. By varying the concentration of PEG-thiol added to the protein (e.g., hemoglobin), it was possible to prepare PEG-hemoglobin RBC that had varying stabilities. The PEG-thiol was prepared by techniques in the literature (such as Harris and Heart Polymer Preprints 32:154 (1991).

PEG-thiol of molecular weight 2000 g/mol was dissolved at a concentration of 1% (0.1 g added to 10 ml) in a 5% hemoglobin solution. The protein-peg solution was sonicated to form the proteinaceous red blood cell substitute as described in Example 14.

EXAMPLE 20

Insoluble Hemoglobin Constructs with Polyethylene Glycol Covalently Attached to the Shell Exterior The IHC were prepared as described in Example 14. Polyethylene glycol of MW10,000 (PEG 10k) was reacted with 1,1'-Carbonyl diimidazole CDI according to techniques available in the literature (Beauchamp et al. *Analytical Biochemistry* 131: 25–33, 1983). The IHC were suspended in 50 mM borate buffer pH 8.0 and PEG-CDI (2 fold molar excess relative to total hemoglobin lysines) was added and the reaction mixture stirred at room temperature for 6 hours. The resulting PEG-IHC were then separated by filtration, washed in saline and resuspended in sterile buffered saline.

EXAMPLE 21

Parameters Affecting Formation of Insoluble Hemoglobin Constructs

Several variables such as protein concentration, temperature, sonication time, acoustic intensity, pH were tested to optimize formation of the IHC.

These materials were prepared from 1%, 2.5%, 5%, and 10% hemoglobin solutions. They were also prepared from mixed protein solution such as hemoglobin and human serum albumin with concentrations again ranging from 1 to 10%. The size and concentrations was determined with a particle counter. The size was found not to significantly vary with starting protein concentration. The number prepared increased with increase starting protein concentration up to about 5%. No significant change in the number was found to occur above that concentration.

Initial vessel temperature were found to be important for optimal preparation of the IHC. Typically the initial reaction temperatures were maintained between 0° and 80° C. The optimal starting temperature was roughly 70° C.

Sonication time was also important factor determining the number of IHC produced per ml. It was found that a sonication time of roughly 30 seconds was good for synthesizing a high concentration of the IHC. Long or shorter sonication times produced less but still a adequate number of IHC.

According to the nomograph provided by the manufacture of the sonicator, the acoustic power rating of the sonicator used in these experiments is approximately 150 watts/cm$^2$. Other power setting were also found to produce a large number of IHC.

EXAMPLE 22

Insoluble Hemoglobin Constructs as Drug Carriers of Oil-Soluble Drugs

The cytotoxic effects of several antineoplastic drugs are greatly enhanced in the presence of oxygen. It is therefore desirable to deliver a drug to a tumor site while increasing oxygen concentration at that site. The hemoglobin microspheres of the present invention allow for that capability. Example 16 above describes the encapsulation of a fluorocarbon liquid in a shell of insoluble hemoglobin. Cytotoxic drugs such as cyclophosphamide, BCNU, Melphalan, taxol, camptothecin, adriamycin, etoposide, and the like, can be dissolved in the fluorocarbon or other suitable oil such as soybean oil and encapsulated into the hemoglobin construct.

Taxol was dissolved in soybean oil (SBO) at a concentration of 5 mg/ml. 3.5 ml of a 5% hemoglobin solution was taken in a to a reaction vessel and 3.5 ml of the SBO/taxol was added to the vessel. The two phase mixture was sonicated as described in Example 16 to obtain crosslinked insoluble hemoglobin shells containing SBO/Taxol.

EXAMPLE 23

Polymeric Shells as Drug Carriers of Water-Soluble Drugs

Several water-soluble drugs are candidates for encapsulation into polymeric shells. As an example methotrexate was dissolved in water at a concentration of 5 mg/ml. One ml of this aqueous solution was emulsified with 4 ml of soybean oil using Pluronic-65 (block copolymer of polyethylene oxide and polypropylene oxide) to form a stable water-in-oil (W/O) microemulsion. 3.5 ml of a 5% hemoglobin solution was overlayered with 3.5 ml of this W/O microemulsion and sonicated for 30 seconds to obtain insoluble hemoglobin constructs containing an encapsulated microemulsion with methotrexate.

EXAMPLE 24

Polymeric Shells as Protein Carriers

Several proteins are candidates for encapsulation into polymeric shells, e.g., hemoglobin, albumin, and the like. For example, as a method of increasing the hemoglobin loading of the IHC, hemoglobin could be encapsulated into the IHC instead of the water soluble drug in Example 23. hemoglobin was dissolved in water at a concentration of 10%. One ml of this aqueous solution was emulsified with 4 ml of soybean oil using Pluronic-65 (block copolymer of polyethylene oxide and polypropylene oxide) to form a stable water-in-oil (W/O) microemulsion. 3.5 ml of a 5% Hemoglobin solution was overlayered with 3.5 ml of this W/O microemulsion containing hemoglobin. The two phase mixture was sonicated for 30 seconds to obtain insoluble hemoglobin constructs containing an encapsulated microemulsion that also contained hemoglobin. This method served to increase the total amount of hemoglobin per microsphere of the IHC and therefore increased the oxygen carrying capacity for bound oxygen.

EXAMPLE 25

In Vivo Administration of Albumin/Fluorocarbon Constructs—Magnetic Resonance Imaging ($^{19}$F-MRI) to Detect Biodistribution Albumin constructs containing perfluorononane were prepared as in Example 17. The final suspension was made up to contain 20% by volume of the fluorocarbon in sterile saline. Two ml of this suspension was injected via the tail vein injection into a ketamine anesthetized Sprague Dawley rat. The in vivo distribution of the fluorocarbon was monitored by $^{19}$F-MRI on a Bruker 500 MHz NMR instrument. The rat was placed into a 10 cm $^{19}$F coil and images obtained using a $T_1$ weighted sequence with TR=1 second, TE=20 milliseconds, and a data matrix of 256×128.

At 1 hour after administration most of the FC was found to accumulate in the liver, lungs, and spleen. Some of the FC could also be detected in the bone marrow. Hemoglobin constructs would be expected to behave in an identical fashion in terms of tissue localization and accumulation. These observations had important implications for the treatment of liver and lung tumors and possibly the treatment of neoplastic cells in the bone marrow with high doses of oxygen in conjunction with the local delivery of a cytotoxic drug or as an adjuvant to radiation therapy.

EXAMPLE 26

In Vivo Administration of Drug Carrying Constructs

Insoluble hemoglobin constructs containing encapsulated Taxol (in SBO) were prepared as in Example 22. The final suspension was made up to contain 20% by volume of the SBO in sterile saline. 2 ml of this suspension was injected via the tail vein injection into a ketamine anesthetized Sprague Dawley rat.

The rat was sacrificed 2 hours after the injection and the liver recovered. The liver was homogenized with a small volume of saline and extracted with ethyl acetate. The extract was lyophilized, dissolved in methanol and injected into an HPLC column. Approximately 15% of the initial dose of unmetabolized taxol was recovered from the liver. This determined the feasibility of targeting antineoplastic drugs to the liver in conjunction with the delivery of oxygen to these sites.

EXAMPLE 27

Acute Blood Replacement Model for Insoluble Hemoglobin Blood Substitute

Anesthetized Sprague-Dawley rats (350–400 g) are catheterized through the external jugular vein. Approximately 70% of their blood volume is removed over a period of 10 minutes. The rats are maintained in this state for 10 additional minutes following which they are reinfused with an iso-oncotic suspension of oxygenated IHC with a $P_{50}$ of 28 mm Hg. The mean arterial pressure, heart rate and breathing rate are continously monitored. The survival of these rats is followed over time.

EXAMPLE 28

Insoluble Hemoglobin Constructs for Reversal of Tissue Ischemia

The ability of the IHC to preferentially deliver oxygen to an ischemic site is exploited. IHC with 'high affinity', i.e., $P_{50}$ <28 mm Hg are useful for this purpose since they will release oxygen only at sites where oxygen gradients are larger than normally encountered in the circulation, that is to say, at an ischemic site. An IHC with $P_{50}$ of 20 mm Hg is utilized for this purpose.

A bilateral carotid occlusion model in a rat is used as a model of 'Stroke' or cerebral ischemia. Both carotid arteries are occluded by temporary ligature in a ketamine anesthetized Sprague-Dawley rat. In the control rat, the ligature is removed after 15 minutes and normal blood flow is resumed. In the experimental rat, 1 ml of a high affinity IHC suspension in saline is infused directly into each carotid artery following external oxygenation of the IHC suspension in an oxygenation device. 24 hours after the treatment, the rats are sacrificed, their brains retrieved, fixed, sectioned and stained with nitro blue tetrazolium (NBT) or trypan blue to determine the degree of cell death. A lower degree of cell death, as determined by tryptan blue staining, is expected in the experimental rat receiving invention IHC.

EXAMPLE 29

Evaluation of In Vivo Circulation Half-Life of Insoluble Hemoglobin Constructs

Anesthetized Sprague-Dawley rats (350–400 g) are catheterized through the external jugular vein. A bolus injection of an iso-oncotic suspension of IHC equivalent to 20% of the animals' blood volume is given through the catheter. Blood is withdrawn at sampling times ranging from 0.25 to 92 hours. Blood samples are centrifuged and plasma observed for signs of hemolysis or presence of soluble hemoglobin. Since the 'microbubbles' of the IHC have a gaseous interior (and are therefore of lower density than water), they rise to the surface of the plasma following centrifugation. The microbubbles are skimmed off, resuspended in saline and counted in a particle counter. The half-lives of IHC in circulation is then determined. Compared to prior art hemoglobin-based blood substitutes, it is expected that invention IHC will demonstrate enhanced circulation half life.

EXAMPLE 30

IHC for Organ Preservation—Preservation of the Rat Heart

The heart is surgically removed from an anesthetized Sprague-Dawley rat and artificially respirated with room air. The heart is immersed in crystalloid medium ('Cardioplegia medium'—CM) having the same composition as IHC (or IHC/FC, or Albumin/FC) preservation medium but without the hemoglobin component. The heart is perfused with the CM for several minutes, cooling it to 11° C. The heart is then preserved with 140 ml of IHC preservation medium for 12 hours at 12° C. The IHC medium is continously perfused through the heart at a low pressure (18 mm Hg) and continously equilibriated with 95% $0_2$/5% $CO_2$. After 12 hours of preservation, the contractile, pump, and energetic functioning of the heart is tested using an isolated working rat heart apparatus.

EXAMPLE 31

Utility of IHC Media in Cardioplegia for Open Heart Surgery

Cardiopulmonary bypass is instituted and oxygenated 'cardioplegia medium' containing IHC (or IHC/FC, or Albumin/FC) as an oxygen carrier, at 4° C., is delivered as a bolus of 500 to 100 ml into the aortic root after appropriate aortic cross-clamping and venting. Additional doses of the cold medium are delivered to the left and right coronary ostia, and in the case of bypass surgeries, the medium is also delivered into the ends of the grafts prior to final anastomoses. The medium is delivered every 15 to 20 min in quantities sufficient to maintain a cool myocardial temperature. After completing the procedure, the aortic clamp is removed and rewarming of the heart started.

EXAMPLE 32

Utility of IHC Media in Angioplasty or Atherectomy

The IHC (or IHC/FC, or Albumin/FC) medium is administered during interventional procedures undertaken to restore flow to obstructed or underperfused regions of an organ. Examples of such procedures are angioplasty and atherectomy. Regional ischemia can be mitigated during balloon inflation of the percutaneous transluminal coronary angioplasty procedure by delivering oxygenated IHC medium at a rate of about 60 ml/min through the central lumen of the dilating balloon catheter. The medium is administered at body temperature and contains, for example, physiologically compatible Ringer's electrolytes and substrates. A dose of oxygen equilibriated IHC medium is infused during each balloon inflation period. A similar procedure is used during the period of balloon inflation in atherectomy procedures which are used to physically remove obstructions in vessels by knife or laser. Infusion of the medium directly into the obstructed vessel during enzymatic thrombolytic procedures could be done to provide oxygenation distal to the obstruction as it is lysed. currently Fluosol-DA is used during some angioplasty procedures; the IHC (or IHC/FC, or Albumin/FC) medium of the present invention would replace Fluosol-DA.

EXAMPLE 33

Synthesis of Dodecafluorononane ($C_9EF_{20}$) Entrapped within a Polymeric Shell A 20 ml glass reaction cell, titanium horn and collar were washed with alcohol and sterile saline prior to synthesis as was all equipment used. In a typical reaction, 3.5 ml of sterile 5% w/v USP (United States Pharmacopaeia) human serum albumin (Alpha Therapeutics Corporation) was added to a reaction cell and the cell attached to the ultrasonic horn (Heat Systems XL2020, 20 KHz, 400 W maximum power). The horn and cell were then submerged in a temperature control bath set to 22° C. Reactions run at 22° C. appeared to be optimum, however product can be synthesized over a wide range of temperatures (0° up to about 40° C.). Temperature control is critical to high yields of material, and the optimum temperature depends on the specific experimental configuration.

Six milliliters of dodecafluorononane ($C_9F_{20}$) was next added, and the ultrasonic source turned on at a power setting of 7. The amount of fluorocarbon added can be varied from less than one ml up to about 13 ml with good yield of protein polymeric shells. The reaction is complete in about 30 seconds. Yields at shorter and longer reaction times appear to be less. The homogeneous suspension produced contains the entrapped dodecafluorononane in protein polymeric shells and is approximately 60% perfluorononane by volume. The aqueous suspension may then be stored in a sterile container at 4° C.

A typical reaction yields a solution that contains approximately $1 \times 10^9$ shells per mL with an average shell diameter of 2 microns with a standard deviation of 1 micron. This synthetic procedure is seen to yield high concentrations of micron-sized biomaterial with narrow size distributions.

EXAMPLE 34

Synthesis of Perfluorotributyl amine ($C_{12}F_{27}N$) or Perfluorotripropyl amine ($C_9F_{21}N$) Entrapped within Polymeric Shells The 5% w/v USP human serum albumin (3.5 ml) and fluoroamine (6 ml) were added to a glass reaction cell and irradiated with high intensity ultrasound. The reaction conditions were a power setting of 7, a bath temperature of 22° C. and a reaction time of approximately 30 seconds. Once again high concentration of both perfluorotripropyl amine [$(C_3F_7)_3N$] and perfluorotributyl amine [$(C_4F_9)_3N$] entrapped in a protein polymeric shell are synthesized ($1 \times 10^9$ shells/mL) with an average diameter of 2 microns.

EXAMPLE 35

Synthesis of Perfluorodecalin ($C_{10}F_{18}$) Entrapped within a Polymeric Shell The 5% w/v USP human serum albumin (3.5 ml) and perfluorodecalin ($C_{10}F_{18}$; 6 ml) were added to a glass reaction cell and irradiated with high intensity ultrasound. The reaction conditions were a power setting of 7, a bath temperature of 22° C. and a reaction time of approximately 30 seconds. High concentration with narrow size distributions of perfluorodecalin contained within a protein polymeric shell were synthesized. Furthermore, since perfluordecalin and perfluorotripropylamine are the major constituents of the FDA approved fluorocarbon, Fluosol DA, the medicinal use of these compounds in medical imaging should be readily accepted by regulatory authorities.

EXAMPLE 36

Synthesis of Perfluoro 15-crown-5 ($C_{10}F_{20}O_5$) Entrapped within a Polymeric Shell The 5% w/v USP human serum albumin (3.5 ml) and the fluorocrown ether ($C_{10}F_{20}O_5$; 6 ml) were added to a glass reaction cell and irradiated with high intensity ultrasound. The reaction conditions were a power setting of 7, a bath temperature of 22° C. and a reaction time of approximately 30 seconds. As before, high concentrations of fluorocrown ether contained in a protein polymeric shell with narrow size distributions are synthesized. In fact this experimental procedure to synthesize fluorocarbon filled polymeric shells was typical for all of the fluorocarbons investigated.

EXAMPLE 37

Synthesis of Perfluoro-t-butylbutene ($C_{10}F_{18}H_2$) Entrapped within a Polymeric Shell The 5% w/v USP human serum albumin (3.5 ml) and $C_{10}F_{18}H_2$ (6 ml) can be added to a glass reaction cell and irradiated with high intensity ultrasound. Reaction conditions comprising a power setting of 7, a bath temperature of 22° C. and a reaction time of approximately 30 seconds would typically be employed. By this procedure, protein polymeric shell having a high concentration of fluoro-t-butylbutane entrapped therein could be synthesized.

EXAMPLE 38

Toxicity of Fluorocarbons Contained within Polymeric Shells

Five rats were injected through a catherized jugular vein with 5 ml of a 20% v/v fluorocarbon suspension (perfluorononane contained in an HSA protein polymeric shell) over 10 minutes. Fluorocarbons in general are nontoxic due the strong fluorine-carbon bonds; indeed, fluorocarbons have been successfully used as FDA approved artificial blood substitutes (Fluosol DA). The rats were harvested at specific times and autopsied. Besides observing the general health of the rat, the liver, spleen, lungs and kidneys were carefully examined. Rats examined at 0.5, 2, 8 and 24 hours were all healthy with no inflamed tissues or organs. The fifth rat is still alive and healthy after 90 days. For comparison, this dose of FDA approved soybean oil in a rat is the $LD_{50}$ amount, further suggesting that fluorocarbons are nontoxic and safe.

EXAMPLE 39

$^{19}F$ Nuclear Magnetic Resonance Spectroscopy of a Neat Fluorocarbon and a Fluorocarbon Entrapped within a Polymeric Shell NMR spectra of the fluorocarbons contained within a protein polymeric shell and neat fluorocarbons were obtained on a Bruker 500 MHz NMR instrument. The instrument was tuned for $^{19}F$ at its resonance frequency of 470.56 MHz. A deuterium solvent was used for locking and all spectra were externally referenced to Freon ($CCl_3F$) at 0 ppm. Perfluorononane and $CDCl_3$ were placed in a 5 mm NMR tube. The spectrum of pure perfluorononane was obtained with two sets of sharp peaks, one at −87 ppm, and the second set of peaks at −127, −128, and −133 ppm.

A suspension of perfluorononane entrapped within HSA protein polymeric shells was resuspended in $D_2O$ and a similar NMR spectrum was obtained. Strong signals were obtained from the 20% v/v fluorocarbon suspension with peaks or resonances at −81, −121, −122 and −126 ppm. The entrapment of the fluorocarbon in the polymeric shell during ultrasonic irradiation resulted in no chemical or structural changes of the perfluorononane. For example, with $C_9F_{20}$ two separate resonance were observed: one corresponding to the $CF_3$ at approximately −80 ppm and the second set of resonances at approximately −125 ppm, corresponding to the $CF_2$ group.

EXAMPLE 40

$^{19}F$ Nuclear Magnetic Resonance Spectroscopy of Fluorocarbons to Measure Local Temperature Variable temperature NMR spectra of fluorocarbons were obtained on a Bruker 500 MHz NMR instrument. The instrument was tuned for $^{19}F$ at its resonance frequency of 470.56 MHz. A deuterium solvent ($d_6$-dimethyl sulfoxide [$d_6$-DMSO]) was used for locking and all spectra were externally referenced to freon ($CCl_3F$) at 0 ppm. Perfluorododecane, which has a melting point of 77° C., and $d_6$-DMSO were placed in a 5 mm NMR tube at room temperature. Fluorine spectra were collected at different temperatures and the linewidths were measured. Linewidth data at −81 ppm, as a function of temperature, are shown below:

| Linewidth @ −81 ppm (Hz) | Temperature (°C.) |
| --- | --- |
| 51.1 | 102 |
| 57.0 | 82 |
| 64.65 | 60 |

The broad spectrum at lower temperatures starts to sharpen as the temperature increases, resulting from the perfluorododecane undergoing its solid to liquid phase transition. The change is sharp and sudden with temperature, as expected for a pure material.

In order to broaden and lower the melting temperature, pentane was added (approximately 2% v/v) to the perfluorododecane. As was seen above, the broad spectra at lower temperatures sharpened as the perfluorododecane goes through its solid to liquid phase transition. Linewidth data as a function of temperature for the perfluorododecane/pentane mixture are shown below:

| Linewidth (Hz) | | Temperature (°C.) |
| --- | --- | --- |
| −82 ppm | −123.3 ppm | |
| 21.26 | 87.17 | 77 |
| 165.89 | 280.50 | 67 |
| 216.6 | 341.2 | 57 |
| 290.77 | 436.15 | 47 |
| 578.27 | 451.33 | 37 |
| 577.62 | 525.11 | 27 |

The resulting perfluorododecane/pentane mixture has a lower melting point that is broadened as expected. With this system, temperature measurements can be made in the range from 27° to 77° C. Thus, given a linewidth, it is possible to determine the local temperature.

An example of use of this technique to determine localized temperatures in vivo involves the injection of protein shells containing fluorocarbon mixtures (e.g., such as described above) with broad melting transitions having temperature-linewidth correlations (which can be empirically obtained). Such a formulation will localize within the liver or spleen and, in addition to serving as a $^{19}$F MRI contrast agent, may simultaneously be utilized to determine locally variant temperatures within the organ (allowing the elucidation of the pathology of significant abnormalities within the tissues).

EXAMPLE 41

$^{19}$F Magnetic Resonance Imaging of Phantoms

Two types of entrapped fluorocarbons contained in polymeric shells were used in this phantom study. Perfluorononane and perfluorotributyl amine contained within HSA protein polymeric shells were synthesized as described in Examples 33 and 34. The synthesized suspension that was 60% fluorocarbon per volume was diluted with saline and 2 milliliters placed in polystyrene tubes. The polystyrene tubes were than placed in a commercially available Siemens 2T MRI instrument (10 cm $^{19}$F coil) operating at 1.5 tesla. $^{19}$F magnetic resonance images of the tubes were taken over a 5 minute period with an echo time (TE) of 10 milliseconds and a time of repetition (TR) of 300 seconds (256×256 matrix).

| Perflurononane Contained in Polymeric Shells | | |
|---|---|---|
| Dilution | [conc], M | Image Clarity |
| 1 | 1.8 | excellent |
| 1/2 | 0.9 | excellent |
| 1/4 | 0.45 | excellent |
| 1/10 | 0.18 | good |
| 1/50 | 0.09 | good |
| 1/100 | 0.02 | marginal |

Good MR phantom images were observed even at low concentrations of perfluorononane entrapped within polymeric shells. Very similar data was observed with polymeric shells that contained perfuorotributyl amine. Only at high dilution (1/100; 0.02M) was the image of poor quality and resolution.

EXAMPLE 42

$^{19}$F Magnetic Resonance Imaging of Liver and Spleen In Vitro 300 gram rats were injected with 2 ml of 20% v/v perfluorononane contained within an HSA protein polymeric shell suspension. At 2 hours and at 5 days, a rat was sacrificed and the liver, spleen, kidneys, and lungs were removed. The entire liver, for example, was then placed in a 4 tesla MRI instrument operating with a 10 cm $^{19}$F coil. $^{19}$F magnetic resonance images of the liver, spleen and kidney were obtained using a $T_1$ weighted sequence with a TR=1 second, a TE=20 milliseconds and a data matrix of 256×128 (i.e., 128 phase encoding steps, 16 signal averages).

$^{19}$F MRI images of the liver showed regions of varying intensity which correlated to varying degrees of liver uptake of the polymeric shells. For example, a dark region corresponding to the portal vein was observed where one would not expect the presence of the perfluorononane-containing polymeric shells since most of the shells are concentrated intracellularly within the RES of the liver.

The average image intensity of the liver scan at two hours after injection was approximately 20–30% higher than that of a scan recorded 5 days after injection, indicating partial dissipation of the perfluorononane, possibly through breakdown of the polymeric shells. Overall, excellent quality images showing liver morphology were obtained, demonstrating the potential of this technique in the diagnosis and localization of abnormal pathology within the liver.

EXAMPLE 43

In Vivo $^{19}$F Magnetic Resonance Imaging of Liver and Spleen

A 150 gram rat was injected with 2 ml of a 20% v/v perfluorononane ($C_9F_{20}$) contained within HSA polymeric shells over 10 minutes. The entire rat was then placed in a 4 tesla MRI instrument operating with a 10 cm $^{19}$F coil. The rat was anaesthetized with ketamine before collecting images. $^{19}$F magnetic resonance images of the entire rat, as well as individual organs such as the liver, spleen and kidney, were obtained using a $T_1$ weighted sequence with a TR=1 second, a TE=20 milliseconds, and a data matrix of 256×128 (i.e., 128 phase encoding steps, 16 signal averages).

Rats were imaged 15 minutes, 2 hours, and 24 hours after injection of the perfluorononane-containing HSA protein polymeric shells. Overall, excellent quality images showing liver and spleen morphology were obtained, demonstrating the potential of this technique in the diagnosis and localization of abnormal pathology within the liver RES containing organs.

EXAMPLE 44

Determination of Local Temperature using In Vivo $^{19}$F Magnetic Resonance Imaging A 300 gram rat is injected with 5 ml of a 20% v/v perfluorododecane/2% pentane (or perfluorononadecanoic acid and 1% cholesterol) contained within HSA polymeric shells over 10 minutes. The rat is then placed in a 15 cm coil (a Siemens 1.5 tesla MRI magnet). A TE of 10 milliseconds and TR of 300 seconds is used to collect the images (256×256 matrix). The rat is anaesthetised with ketamine before collecting data. The liver and spleen are imaged over a 15 minute period, by taking a 5 millimeter slice thickness. Data are collected at room temperature and at approximately 37° C., by wrapping the subdued rat in a heating pad.

EXAMPLE 45

In Vivo Oxygen Determination Using $^{19}$F Magnetic Resonance Imaging

A 300 gram rat is injected with 5 ml of 20% v/v perfluorononane contained within HSA polymeric shells over 10 minutes. The rat is next placed in a 15 cm coil (a Siemens 1.5 tesla MRI magnet). ATE of 70 milliseconds and TR of 3 seconds is used to collect the images (256×256 matrix). The rat is placed in a restraining harness before collecting data. The rat is first put in an oxygen chamber to increase oxygen metabolism, and the linewidth and image are collected. The rat is next injected with ketamine, to reduce the consumption of oxygen, and again the linewidth and image are collected. The linewidth and the intensity of the image are observed to change, corresponding to the amount of dissolved oxygen in the rat. The largest linewidth is observed at higher oxygen concentrations. The liver and spleen are imaged over 15 minutes taking a 5 millimeter slice thickness. Two data sets are collected, one at room temperature and another at 37° C., by wrapping the anaesthetized rat in a heating pad.

EXAMPLE 46

Preparation of Taxol Particles

Crystals of taxol (Sigma Chemical) were ground in a ball mill until particles of solid taxol were obtained having a size less than 10 microns. Size of particles were determined by suspending the particles in isotonic saline and counting with the aid of a particle counter (Elzone, Particle Data). Grinding was continued until 100% of the particles had a size less than 5 microns. The preferred particle size for intravenous delivery is less than 5 microns and most preferably less than 1 micron.

Alternatively, particles of taxol were obtained by sonicating a suspension of taxol in water until all particles were below 10 microns.

Taxol particles less than 10 microns can also be obtained by precipitating taxol from a solution of taxol in ethanol by adding water until a cloudy suspension is obtained. Optionally, the solution of taxol can be sonicated during the water addition, until a cloudy suspension is obtained. The resulting suspension is then filtered and dried to obtain pure taxol particles in the desired size range.

Fine particles of taxol were prepared by spray drying a solution of taxol in a volatile organic such as ethanol. The solution was passed through an ultrasonic nozzle that formed droplets of ethanol containing taxol. As the ethanol evaporated in the spray drier, fine particles of taxol were obtained. Particle size can be varied by changing the concentration of taxol in ethanol, adjusting the flow rate of liquid through the nozzle and power of sonication.

EXAMPLE 47

Synthesis of Paramagnetic Cations Bound to Polyanions

Synthesis of Gd-alginates can be carried out, for example, by dispersing the alginate in a solution of $GdCl_3$. For example, small spherical particles of Gd-alginate suitable for intravascular injection may be synthesized by ultrasonic irradiation of a solution containing Gd ions (e.g., $GdCl_3$) and adding small quantities of Na-alginate solution. The alginate is dispersed into the solution of Gd ions by the ultrasonic irradiation, and crosslinked by the multivalent Gd ions, producing micron sized particles of Gd-alginate. Besides ultrasonic irradiation, low or high speed mixing can also be used.

Alternatively, a solution of Na-alginate is overlaid or layered on an immiscible organic solvent or oil (e.g., soybean oil, sunflower oil, toluene, methylene chloride, chloroform, and the like). The liquids are subjected to ultrasonic irradiation whereby the alginate-containing aqueous phase is dispersed into the organic phase, then a solution of multivalent ions (e.g., $GdCl_3$, $MnCl_3$, $FeCl_3$, and the like) is added. The Na-alginate is thereby crosslinked, producing tiny spherical particles of Gd-alginate which are suitable for use as an MRI contrast agent following intravascular injection. Essentially any synthetic technique using alginates and multivalent cations can be used to form spheres, fibers, plates, blocks, and the like.

While the invention has been described in detail with reference to certain preferred embodiments thereof, it will be understood that modifications and variations are within the spirit and scope of that which is described and claimed.

That which is claimed is:

1. A method for the preparation of blood substitutes for in vivo delivery, said method comprising subjecting aqueous medium containing oxygen binding protein to high intensity ultrasound conditions for a time sufficient to promote crosslinking of said oxygen binding protein by disulfide bonds to form a polymeric shell;

wherein the largest cross-sectional dimension of shell is no greater than about 10 microns.

2. A method for the delivery of a blood substitute to a subject, said method comprising administering to said subject an effective amount of blood substitute prepared according to the method of claim 1.

3. The method according to claim 1, wherein said oxygen binding protein is selected from hemoglobin, myoglobin, or a mixture thereof.

4. The method according to claim 1, wherein said oxygen binding protein is hemoglobin.

5. A method for the preparation of blood substitutes for in vivo delivery, said method comprising subjecting aqueous medium containing biocompatible material and a blood substitute to high intensity ultrasound conditions for a time sufficient to promote crosslinking of said biocompatible material by disulfide bonds;

wherein said blood substitute is substantially completely contained within a polymeric shell, and wherein the largest cross-sectional dimension of said shell is no greater than about 10 microns.

6. The method according to claim 5, wherein said biocompatible material is a naturally occurring polymer, a synthetic polymer, or a combination thereof, wherein said polymer, prior to crosslinking, has covalently attached thereto sulfhydryl groups or disulfide linkages.

7. The method according to claim 6, wherein said naturally occurring polymer is selected from proteins containing sulfhydryl groups and/or disulfide groups, polypeptides containing sulfhydryl groups and/or disulfide groups, lipids containing sulfhydryl groups and/or disulfide groups, polynucleic acids containing sulfhydryl groups and/or disulfide groups, or polysaccharides containing sulfhydryl groups and/or disulfide groups.

8. The method according to claim 7, wherein said protein is selected from hemoglobin, myoglobin, albumin, insulin, lysozyme, immunoglobulins, $\alpha$-2-macroglobulin, fibronectin, vitronectin, fibrinogen, or combinations of any two or more thereof.

9. The method according to claim 8, wherein said protein is albumin.

10. The method according to claim 8, wherein said protein is hemoglobin.

11. The method according to claim 8, wherein said protein is a combination of albumin and hemoglobin.

12. A method for the delivery of a blood substitute to a subject, said method comprising administering to said subject an effective amount of blood substitute prepared according to the method of claim 5.

13. The method according to claim 4, wherein said hemoglobin is modified with an allosteric effector.

14. The method according to claim 13, wherein said allosteric effector is selected from inositol hexaphosphate, 2,3-bisphosphoglycerate, a di or monoaspirin ester, or combinations of any two or more thereof.

15. The method according to claim 14, wherein said diaspirin ester is 3,5-bis(dibromosalicyl)fumarate.

16. The method according to claim 3, wherein said protein is myoglobin.

17. The method according to claim 1, wherein said oxygen binding protein is combined with a second protein selected from albumin, insulin, lysozyme, an immunoglobulin, alpha-2-macroglobulin, fibronectin, vitronectin, fibrinogen, or combinations of any two or more thereof.

18. The method according to claim 17, wherein said second protein is albumin.

19. The method according to claim 17 wherein said second protein is albumin and said oxygen binding protein is hemoglobin.

20. The method according to claim 1, wherein said polymeric shell is modified by a suitable agent, wherein said suitable agent is selected from a synthetic polymer, a phospholipid, a protein, a polysaccharide, a surface active agent, a chemical modifying agent, or combination thereof, wherein said suitable agent is associated with said polymeric shell through an optional covalent linkage.

21. The method according to claim 1, wherein said polymeric shell is suspended in a biocompatible medium, and wherein said biocompatible medium is selected from water, buffered aqueous media, saline, buffered saline, a solution of amino acids, a solution of proteins, a solution of sugars, a solution of vitamins, a solution of carbohydrates, a solution of synthetic polymers, a lipid-containing emulsion, or combinations of any two or more thereof.

22. The method according to claim 1, wherein said aqueous medium containing the oxygen binding protein contains a biologic and wherein after crosslinking, said biologic is completely contained within said polymeric shell.

23. The method according to claim 22, wherein said biologic within said shell is dissolved or suspended in a biocompatible dispersing agent.

24. The method according to claim 7, wherein said polysaccharides are selected from an alginate, a polymannuronic acid, a polymannuronate, a hyaluronic acid, a hyaluronate, heparin, dextran, chitosan, chitin, cellulose, starch, glycogen, guar gum, locust bean gum, levan, inulin, cyclodextrin, agarose, xanthan gum, carrageenan, heparin, pectin, gellan gum, scleroglucan, or combinations of any two or more thereof.

25. The method according to claim 24, wherein said alginate is a high M-content alginate.

26. The method according to claim 6, wherein said synthetic polymer is selected from a synthetic polyamino acid containing cysteine residues and/or disulfide groups, a synthetic polypeptide containing sulfhydryl groups and/or disulfide groups, a polyvinyl alcohol modified to contain free sulfhydryl groups and/or disulfide groups, a polyhydroxyethyl methacrylate modified to contain free sulfhydryl groups and/or disulfide groups, a polyacrylic acid modified to contain free sulfhydryl groups and/or disulfide groups, polyethyloxazoline modified to contain free sulfhydryl groups and/or disulfide groups, a polyacrylamide modified to contain free sulfhydryl groups and/or disulfide groups, polyvinyl pyrrolidinone modified to contain free sulfhydryl groups and/or disulfide groups, a polyalkylene glycol modified to contain free sulfhydryl groups and/or disulfide groups, as well as mixtures of any two or more thereof.

27. The method according to claim 5, wherein said polymeric shell is modified by a suitable agent, wherein said suitable agent is selected from a synthetic polymer, a phospholipid, a protein, a polysaccharide, a surface active agent, a chemical modifying agent, or combination thereof, wherein said suitable agent is associated with said polymeric shell through an optional covalent linkage.

28. The method according to claim 5, wherein said blood substitute is selected from hemoglobin, myoglobin, or mixtures thereof.

29. The method according to claim 28, wherein said blood substitute is hemoglobin.

30. The method according to claim 29, wherein said hemoglobin is modified with an allosteric effector.

31. The method according to claim 30, wherein said allosteric effector is selected from inositol hexaphosphate, 2,3-bisphosphoglycerate, a di or monoaspirin ester, or combinations of any two or more thereof.

32. The method according to claim 31, wherein said diaspirin ester is 3,5-bis(dibromosalicyl) fumarate.

33. The method according to claim 28, wherein said blood substitute is myoglobin.

34. The method according to claim 5, wherein said blood substitute is selected from perfluorodecalin or perfluorotripropylamine.

35. The method according to claim 5, wherein said blood substitute is crosslinked.

36. The method according to claim 5, wherein said blood substitute within said shell is dissolved or suspended in a biocompatible dispersing agent.

37. The method according to claim 5, wherein said polymeric shell containing said blood substitute is suspended in a biocompatible medium, and wherein said biocompatible medium is selected from water, buffered aqueous media, saline, buffered saline, a solution of amino acids, a solution of protein, a solution of sugars, a solution of vitamins, a solution of carbohydrates, a solution of synthetic polymers, a lipid-containing emulsion, or combinations of any two or more thereof.

38. The method according to claim 10, wherein a phospholipid bilayer is formed around the crosslinked hemoglobin shell.

39. The method according to claim 38, wherein said phospholipid bilayer is formed from charged lipids, nonionic lipids, polymerizable lipids, or combinations of any two or more thereof.

40. The method according to claim 39, wherein said charged lipid is selected from phosphatidyl choline, phosphatidyl ethanol amine, phosphatidyl serine, phosphatidyl inositol, phosphatidyl glycerol, sphingomyelin, dimyristoylphosphatidic acid, dipalmitoyl phosphatidic acid, a sarcosinate (sarcosinamide), a betaine, a monomeric and dimeric alkyd, or combinations of any two or more thereof.

41. The method according to claim 39, wherein said nonionic lipid is selected from a polyethylene fatty acid ester, a polyethylene fatty acid ether, a diethanolamide, a long chain acyl hexosamide, a long chain acyl amino acid amide, a long chain amino acid amine, a polyoxyethylene sorbitan ester, a polyoxy glycerol mono- and di-ester, a glycerol mono- and di-stearate, a glycerol mono- and di-oleate, a glycerol mono- and di-palmitate, or combinations of any two or more thereof.

42. The method according to claim, 39, wherein said photopolymerizable lipid is selected from phosphatidyl choline, phosphatidyl ethanol amine, phosphatidyl serine, phosphatidyl glycerol, dimyristoylphosphatidic acid, dipalmitoyl phosphatidic acid, a lipid with native polymerizable unsaturation, or combinations of any two or more thereof.

43. The method according to claim 42, wherein said lipid with native polymerizable unsaturation comprises an unsaturated phosphatidyl choline with diacetylene groups, an unsaturated phosphatidyl choline with conjugated diene groups, or combinations of any two or more thereof.

44. The method according to claim 39, wherein said crosslinkable lipid comprises one or more derivatives of a phosphatidyl choline esterified with lipoic acid.

* * * * *